US010607099B2

(12) United States Patent
Cai et al.

(10) Patent No.: US 10,607,099 B2
(45) Date of Patent: Mar. 31, 2020

(54) METHODS AND SYSTEMS FOR IMAGING PERFORMANCE ANALYSIS

(71) Applicant: SHENZHEN UNITED IMAGING HEALTHCARE CO., LTD., ShenZhen, Guangdong (CN)

(72) Inventors: Pengfei Cai, Shanghai (CN); Feifei Dou, Shanghai (CN); Yanyan Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 202 days.

(21) Appl. No.: 15/721,775

(22) Filed: Sep. 30, 2017

(65) Prior Publication Data
US 2019/0034749 A1 Jan. 31, 2019

Related U.S. Application Data

(63) Continuation of application No. PCT/CN2017/095077, filed on Jul. 29, 2017.

(51) Int. Cl.
*G06K 9/00* (2006.01)
*G06K 9/32* (2006.01)
(Continued)

(52) U.S. Cl.
CPC .......... *G06K 9/3233* (2013.01); *A61B 6/5223* (2013.01); *A61B 6/584* (2013.01);
(Continued)

(58) Field of Classification Search
CPC ........... G06K 9/3232; G06T 7/11; G06T 7/66; G06T 2207/10081; A61B 6/5223; A61B 6/584; A61B 6/032
See application file for complete search history.

(56) References Cited

U.S. PATENT DOCUMENTS 8,102,392 B2 * 1/2012 Yamagata ................ A61B 6/12
345/420
9,857,443 B2 * 1/2018 Tadic .................... G01R 33/387
(Continued)

FOREIGN PATENT DOCUMENTS

CN 103340643 A 10/2013
CN 103471811 A 12/2013
(Continued)

OTHER PUBLICATIONS

International Search Report in International Application No. PCT/CN2017/095077 dated May 7, 2018, 6 pages.
(Continued)

Primary Examiner — Gregory M Desire
(74) Attorney, Agent, or Firm — Metis IP LLC

(57) ABSTRACT

A method for analyzing performance of an imaging device including a scanner with a phantom includes receiving image data related to a scanning, by the scanner, of a first part of the phantom including at least part of a first test component. The method also includes obtaining at least one positioning parameter indicative of a positioning manner of the phantom during the scanning. The method further includes generating a first test image based on the received image data and determining a first region of interest (ROI) related to the first test component in the first test image based on the at least one positioning parameter.

20 Claims, 20 Drawing Sheets

(51) Int. Cl.
*G06T 7/11* (2017.01)
*A61B 6/00* (2006.01)
*G06T 7/66* (2017.01)
*A61B 6/03* (2006.01)

(52) U.S. Cl.
CPC .................. *G06T 7/11* (2017.01); *G06T 7/66* (2017.01); *A61B 6/032* (2013.01); *G06T 2207/10081* (2013.01); *G06T 2207/10084* (2013.01); *G06T 2207/10088* (2013.01); *G06T 2207/10104* (2013.01); *G06T 2207/10108* (2013.01); *G06T 2207/30* (2013.01)

(56) References Cited

U.S. PATENT DOCUMENTS

| | | | |
|---|---|---|---|
| 9,865,060 B2* | 1/2018 | Mukumoto | A61B 6/5205 |
| 10,215,818 B2* | 2/2019 | Reykowski | G01R 33/3621 |
| 2004/0156480 A1 | 8/2004 | Gerwin et al. | |
| 2007/0258559 A1* | 11/2007 | Hur | A61B 6/481 378/16 |
| 2017/0311921 A1* | 11/2017 | Feuerlein | A61B 6/032 |
| 2018/0096477 A1* | 4/2018 | Avila | G06T 7/0002 |

FOREIGN PATENT DOCUMENTS

| | | |
|---|---|---|
| CN | 104287761 A | 1/2015 |
| JP | 2016036515 A | 3/2016 |

OTHER PUBLICATIONS

Written Opinion in International Application No. PCT/CN2017/095077 dated May 7, 2018, 3 pages.

* cited by examiner

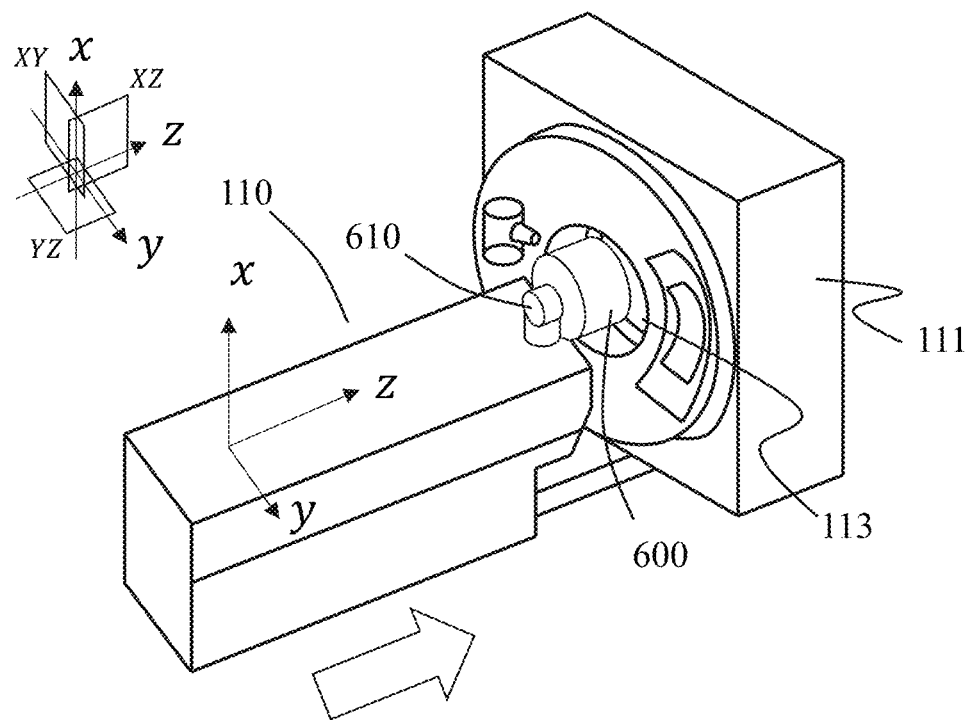
FIG. 6-A
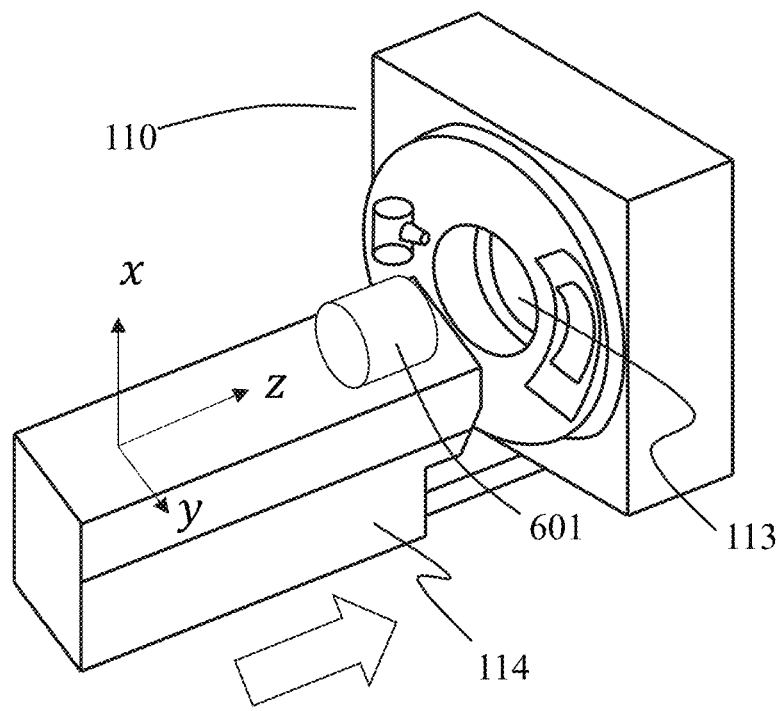
FIG. 6-B

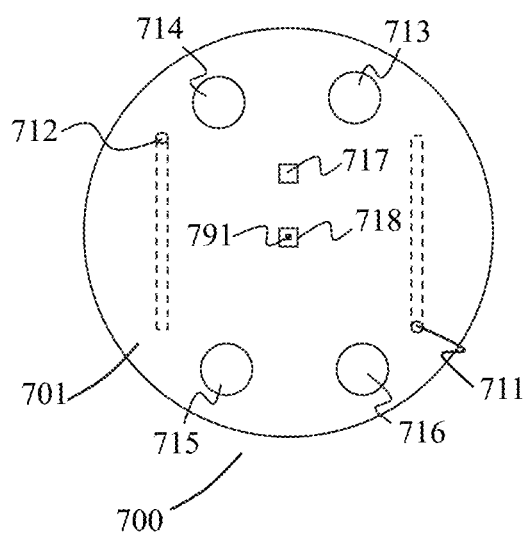
FIG. 7-A
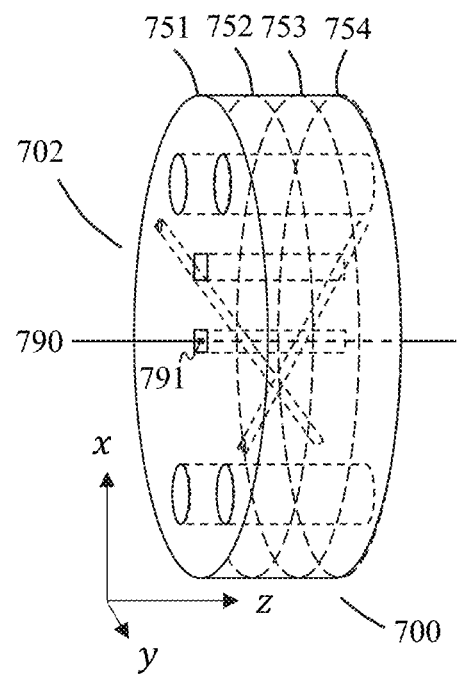
FIG. 7-B
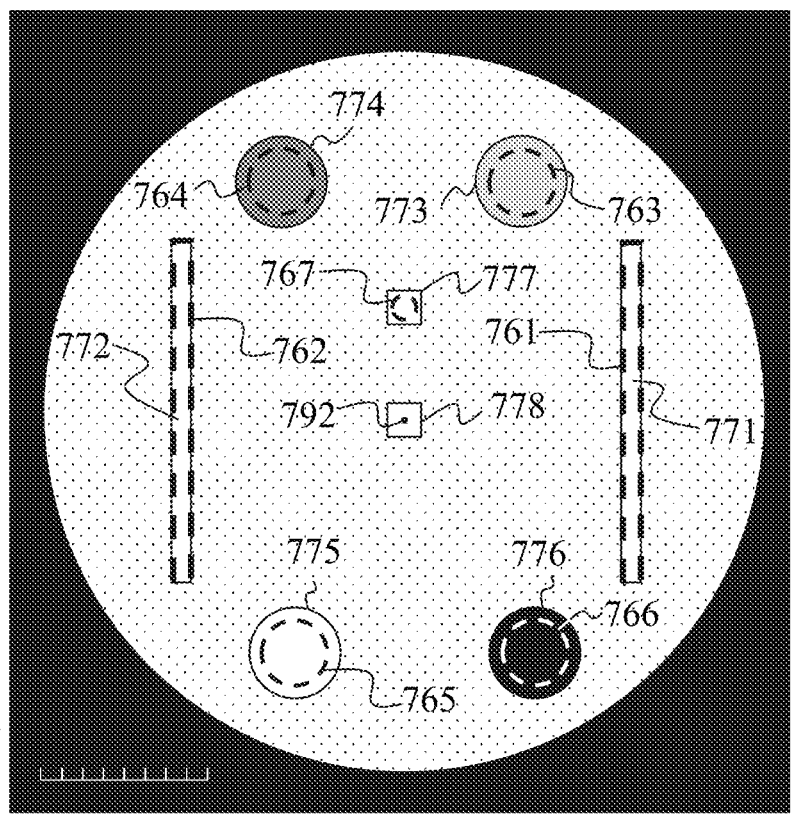
FIG. 7-C

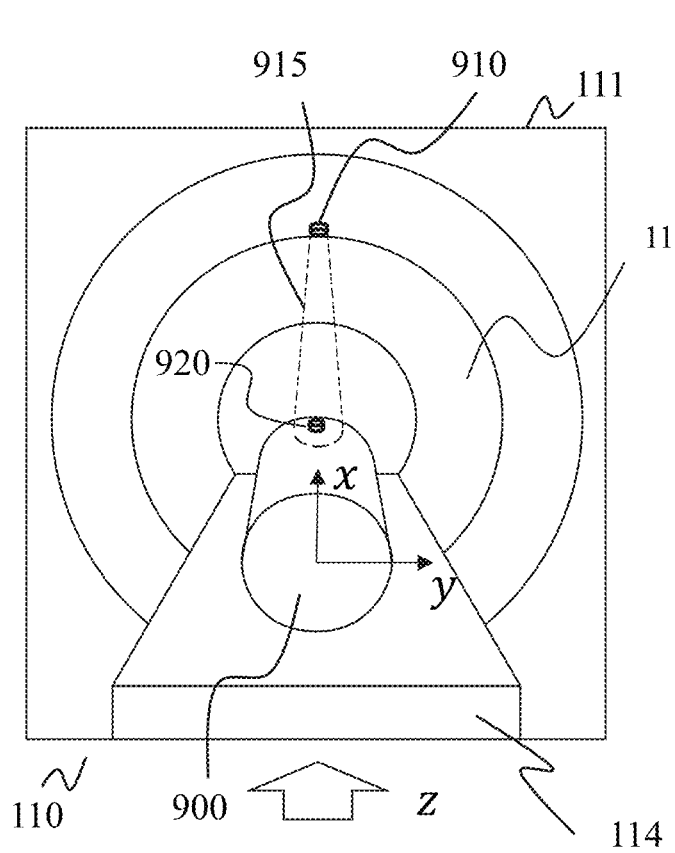
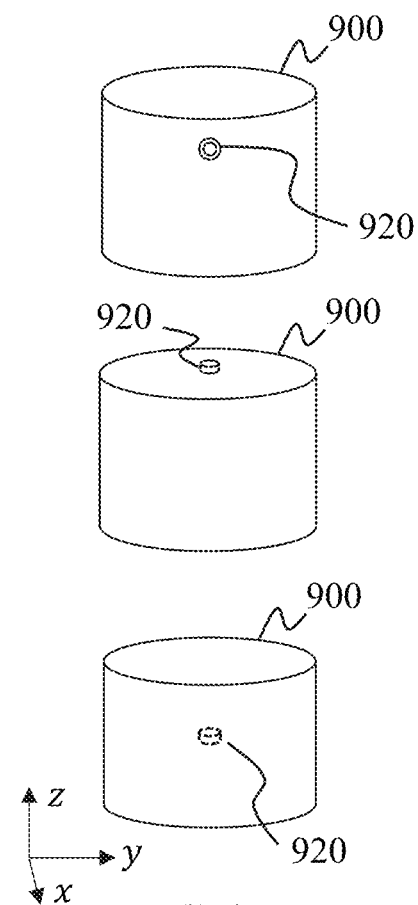
FIG. 9-A
FIG. 9-B
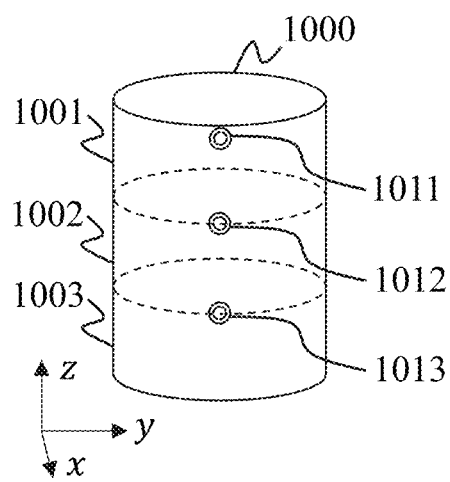
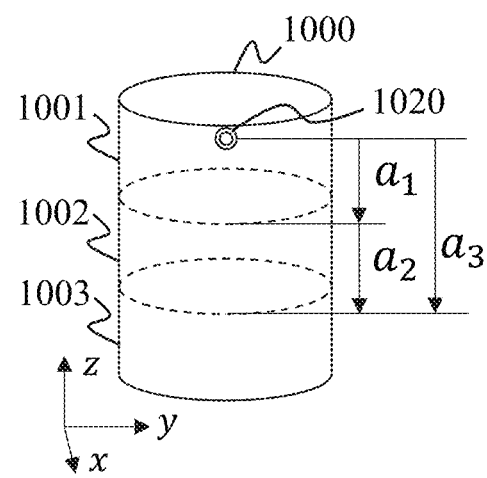
FIG. 10-A
FIG. 10-B

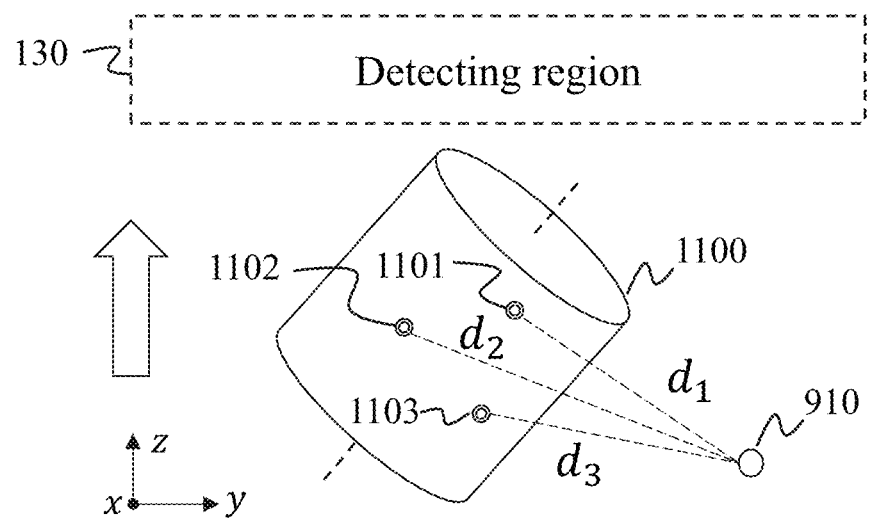
FIG. 11-A
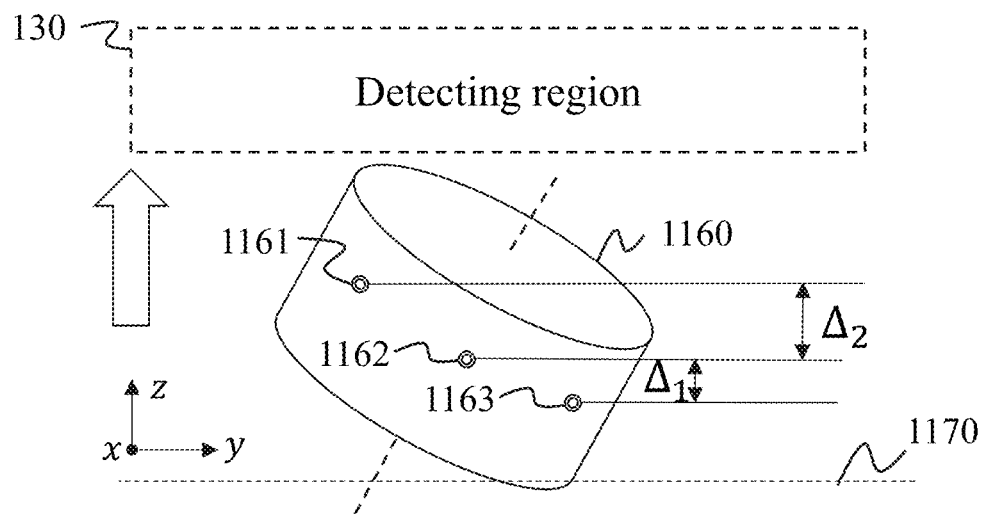
FIG. 11-B

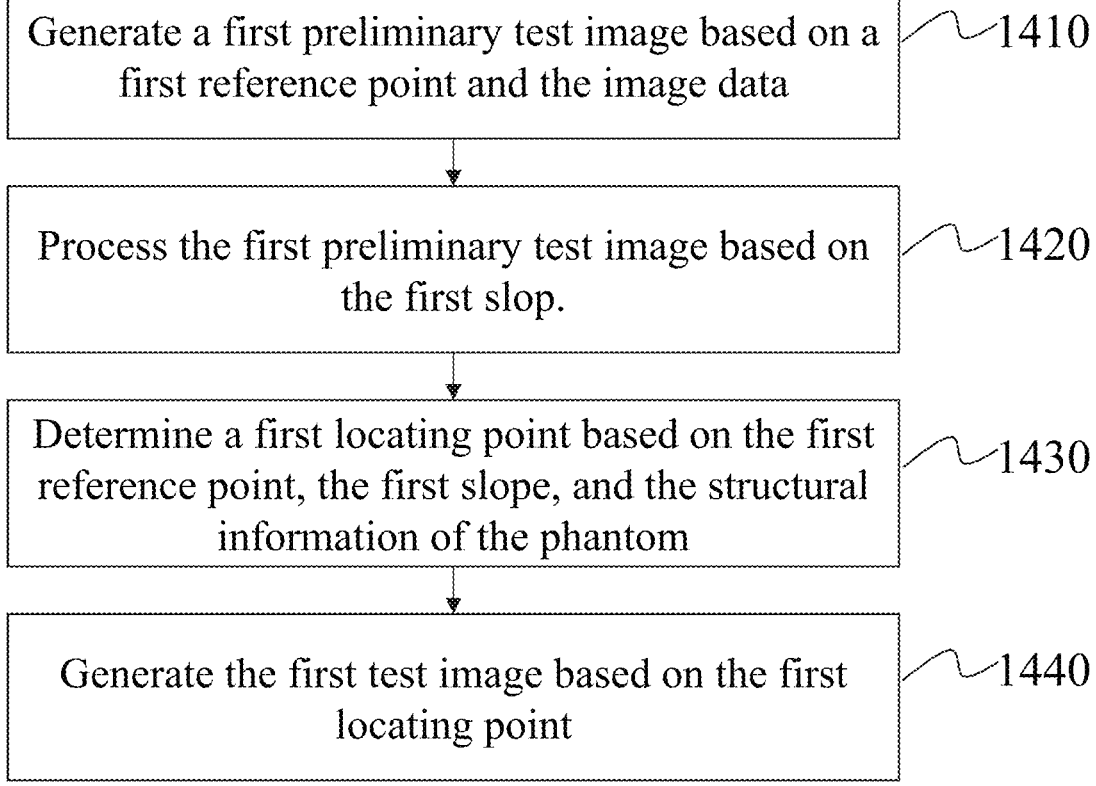
FIG. 14-A
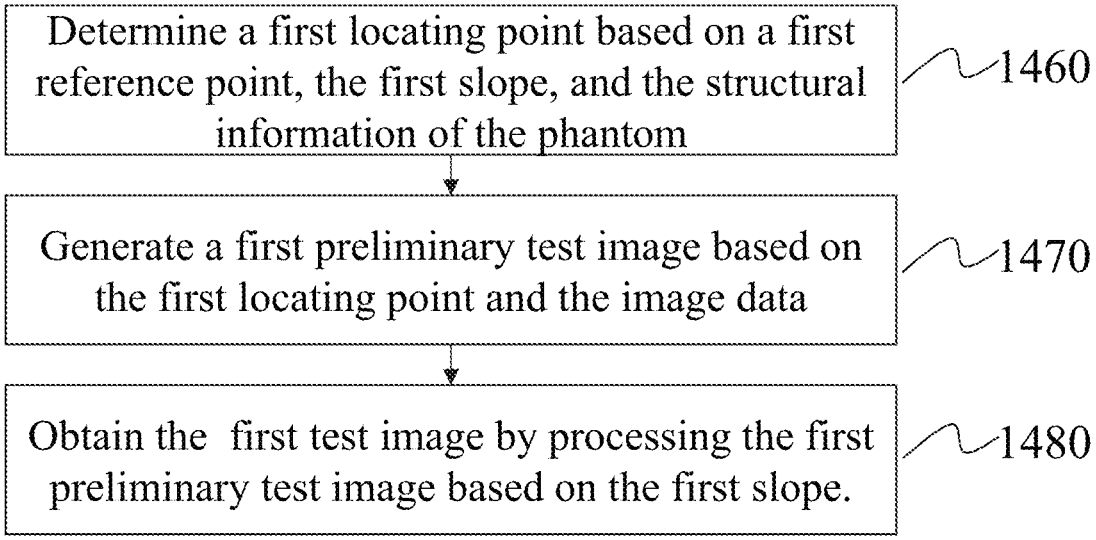
FIG. 14-B

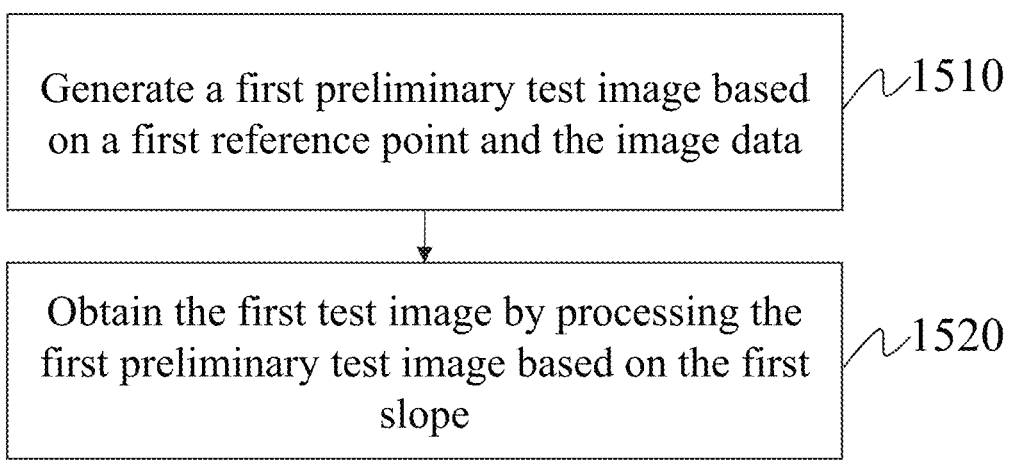
FIG. 15-A
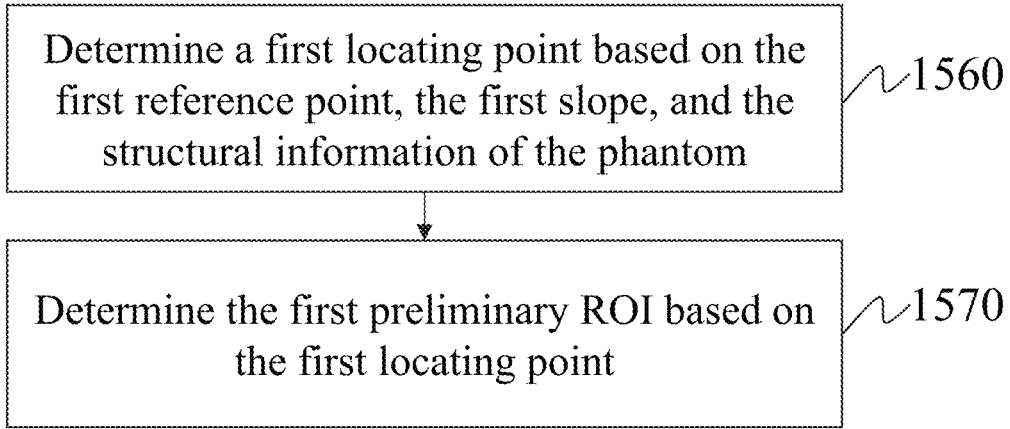
FIG. 15-B

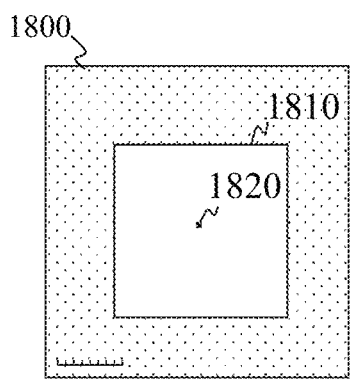
FIG. 18-A
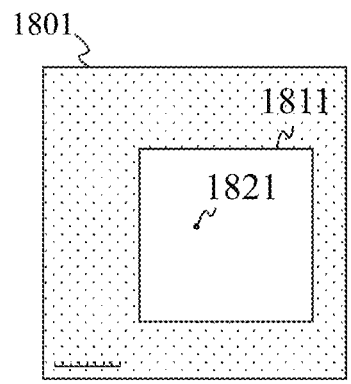
FIG. 18-B
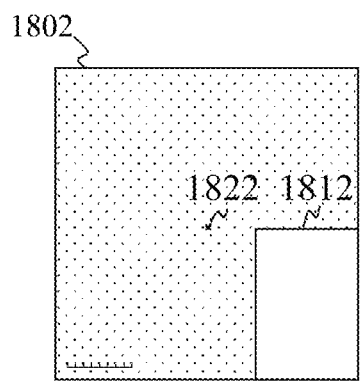
FIG. 18-C

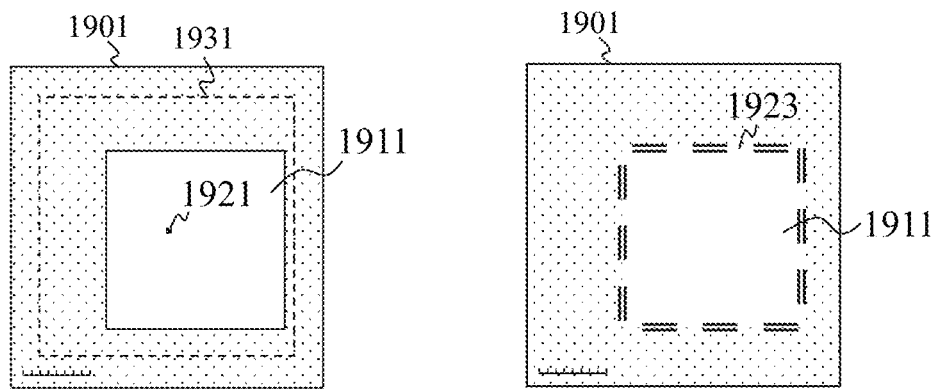
FIG. 19-A
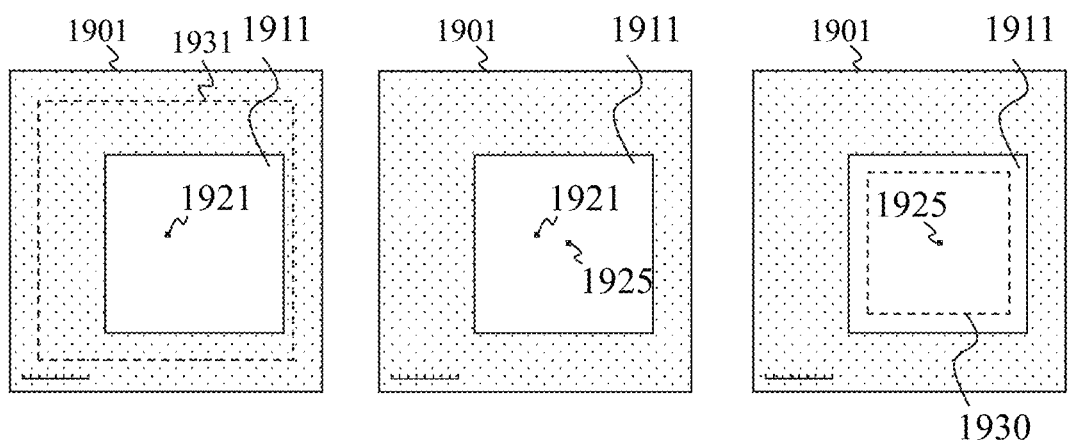
FIG. 19-B

2100

Generate a third test image showing a scanned portion of a third test module based on the received image data and the at least one positioning parameter — 2120

Determine a third ROI relating to the third test component in the third image based on the at least one positioning parameter — 2130

Analyze performance of the imaging device based on the first ROI and the third ROI — 2140

FIG. 21

METHODS AND SYSTEMS FOR IMAGING PERFORMANCE ANALYSIS

CROSS-REFERENCE TO RELATED APPLICATIONS

This application is a continuation of International Application No. PCT/CN2017/095077, filed on Jul. 29, 2017. The disclosure of the above-referenced application is incorporated herein by reference in its entirety.

TECHNICAL FIELD

The present invention generally relates to imaging performance analysis of an imaging device, and more specifically to a method and apparatus for automatically or semi-automatically acquiring and analyzing imaging quality parameters of an imaging device.

BACKGROUND

The imaging performance analysis of an imaging system may be performed for monitoring the working state of a scanner of the imaging system, assessing the effectiveness of an algorithm or an imaging technique adopted by the imaging system, and determining one or more specific parameters (e.g., parameters for scanning, data processing, image reconstruction, image rendering) used by the imaging system. During the imaging performance analysis, a phantom is usually scanned by the scanner. The imaging data may be generated and used to determine the performance of the scanner.

SUMMARY

According to an aspect of the present disclosure, a method may include receiving image data related to a scanning, by the scanner, of a first part of a phantom including at least part of a first test component. The method also includes obtaining at least one positioning parameter indicative of a positioning manner of the phantom during the scanning. The method further includes generating a first test image based on the received image data and determining a first region of interest (ROI) related to the first test component in the first test image based on the at least one positioning parameter.

In some embodiments, the phantom may further include one or more positioning modules. The method may further include determining, based on the one or more positioning modules, at least one of the first part of the phantom or the at least one positioning parameter.

In some embodiments, the determining the first ROI based on the image data and the at least one positioning parameter may include: generating the first test image based on the image data and the at least one positioning parameter, wherein the first test image shows a scanned portion of a first test module of the phantom, and the first test module includes the first test component; determining a first preliminary ROI in the first test image, the first preliminary ROI including an image region representing a scanned portion of the first test component; and determining the first ROI based on the first preliminary ROI.

In some embodiments, the determining the first preliminary ROI in the first test image may include: determining a first locating point based on the at least one positioning parameter and structural information of the phantom indicating the location of the first test component in the phantom; and determining the first preliminary ROI based on the first locating point, wherein the first locating point is set as a reconstruction center of the first test image.

In some embodiments, the generating the first test image based on the image data and the at least one positioning parameter may include: determining a first locating point based on the at least one positioning parameter and structural information of the phantom indicating the location of the first test component in the phantom; and generating the first test image based on the first locating point, wherein the first locating point is set as a reconstruction center of the first test image.

In some embodiments, the at least one positioning parameter may include a first reference point corresponding to a first point within the first part of the phantom and a first slope of the phantom relative to a first direction. The cross-section of the phantom at which the first point locates may cut through the first test component. The first test module may include a plurality of first test components. The method may further include: generating a first cross-sectional image of the phantom based on the first reference point, the first slope, and the image data, wherein the first reference point is set as a reconstruction center of the first cross-sectional image and the first cross-sectional image is designated as the first test image; determining, for each of the first test components, a second locating point within the first test image based on the first reference point, the first slope, and structural information of the phantom indicating the location of the each of the first test components in the phantom; generating, for the each of the first test components, a first preliminary ROI based on the corresponding second locating point, and obtaining, for the each of the first test components, a first ROI based on the first preliminary ROI; and analyzing the performance of the imaging device based on the obtained first ROIs for the plurality of the first test components.

In some embodiments, the scanned first part of the phantom may further include at least part of a second test component. The method may further include: obtaining a second test image showing a scanned portion of a second test module, the second test module including the second test component; determining a second ROI relating to the second test component in the second image based on the at least one positioning parameter; and analyzing the performance of the imaging device based on the first ROI and the second ROI.

In some embodiments, the phantom may further include a second part that includes a third test component, and the received image data may relate to the scanning of both the first part and the second part of the phantom. The method may further include generating a third test image based on the received image data and the at least one positioning parameter. The method may also include determining a third ROI relating to the third test component in the third test image based on the at least one positioning parameter and analyzing the performance of the imaging device based on the first ROI and the third ROI.

In some embodiments, the at least one positioning parameter may include a first reference point corresponding to a first point within the first part of the phantom, a first slope of the phantom relative to a first direction, a second slope of the phantom relative to a second direction, and a third slope of the phantom relative to a third direction. The determining of the third ROI based on the at least one positioning parameter may include: determining a second reference point corresponding to a point within the second part of the phantom based on the first reference point, the second slope, the third slope, and structural information of the phantom indicating the location of the second point relative to the first point; and generating the third test image based on the second reference point and the first slope. The cross-section of the phantom at which the second point locates may cut through the third test component.

According to another aspect of the present disclosure, a system may include at least one storage device storing instructions and at least one processor being communication with the at least one storage device. When executing the instructions, the at least one processor may be configured to cause the system to receive image data related to a scanning, by a scanner of the imaging device, of a first part of a phantom including at least part of a first test component. The at least one processor may also be configured to cause the system to obtain at least one positioning parameter indicative of a positioning manner of the phantom during the scanning and generate a first test image based on the received image data. The at least one processor may further be configured to cause the system to determine a first region of interest (ROI) relating to the first test component in the first test image based on the at least one positioning parameter.

According to yet another aspect of the present disclosure, a non-transitory computer-readable medium may embody a computer program product including instructions configured to cause a computing device to perform a method comprising receiving image data related to a scanning, by the scanner, of a first part of a phantom including at least part of a first test component. The method also includes obtaining at least one positioning parameter indicative of a positioning manner of the phantom during the scanning. The method further includes generating a first test image based on the received image data and determining a first region of interest (ROI) related to the first test component in the first test image based on the at least one positioning parameter.

BRIEF DESCRIPTIONS OF THE DRAWINGS

Figure 8:
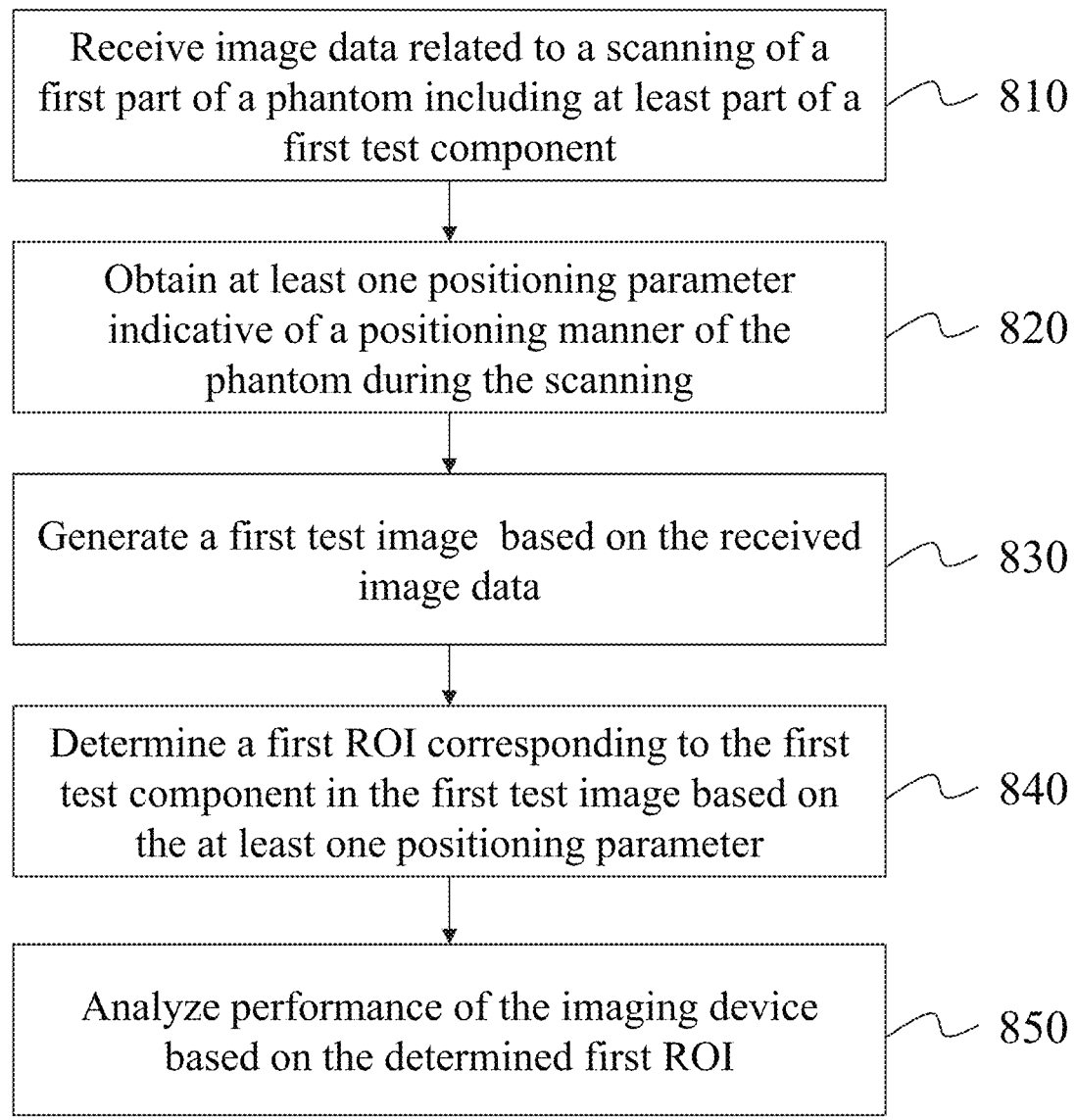
Figure 12:
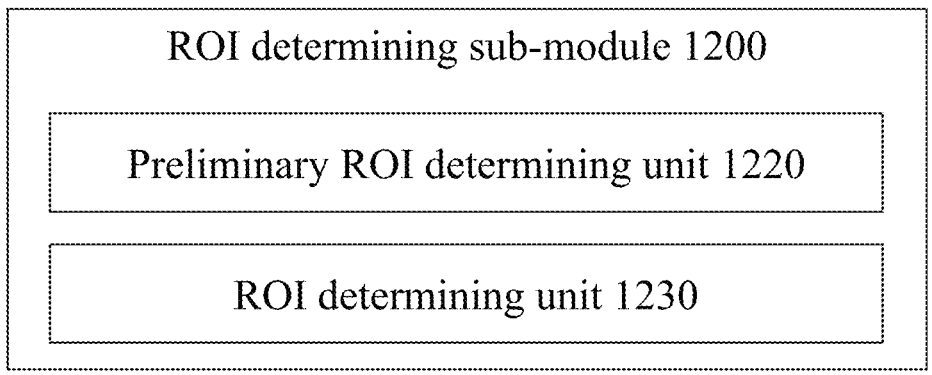
Figure 13:
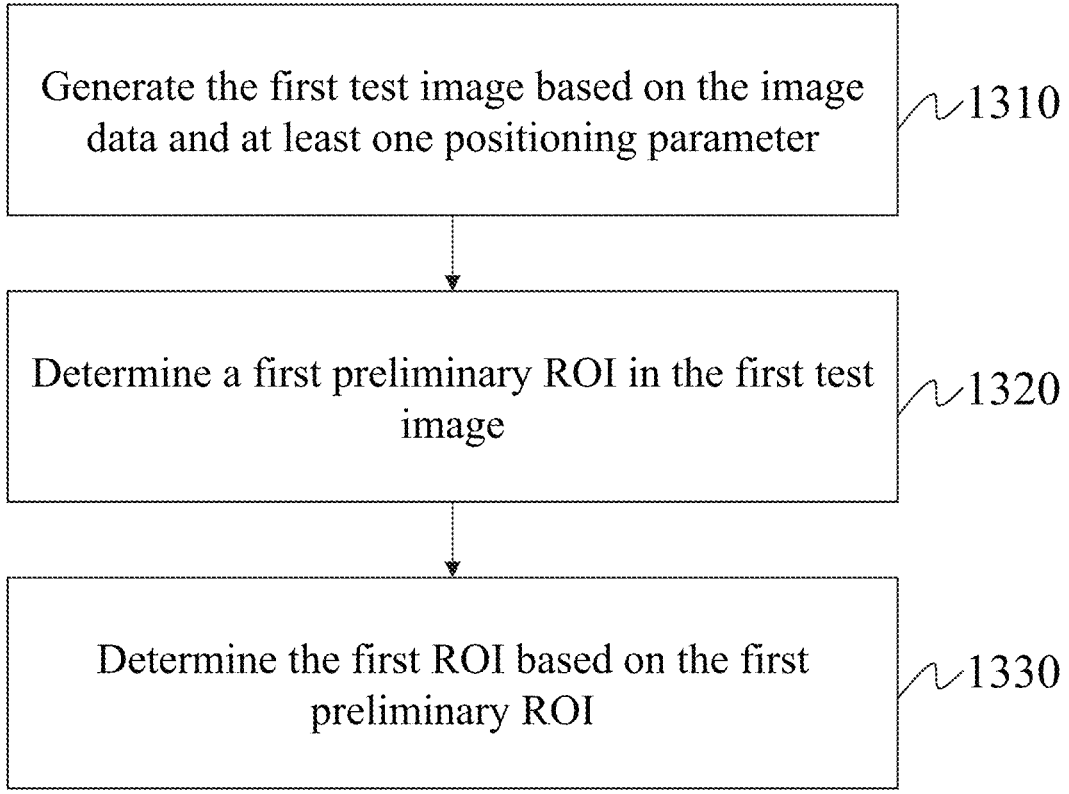
Figure 16:
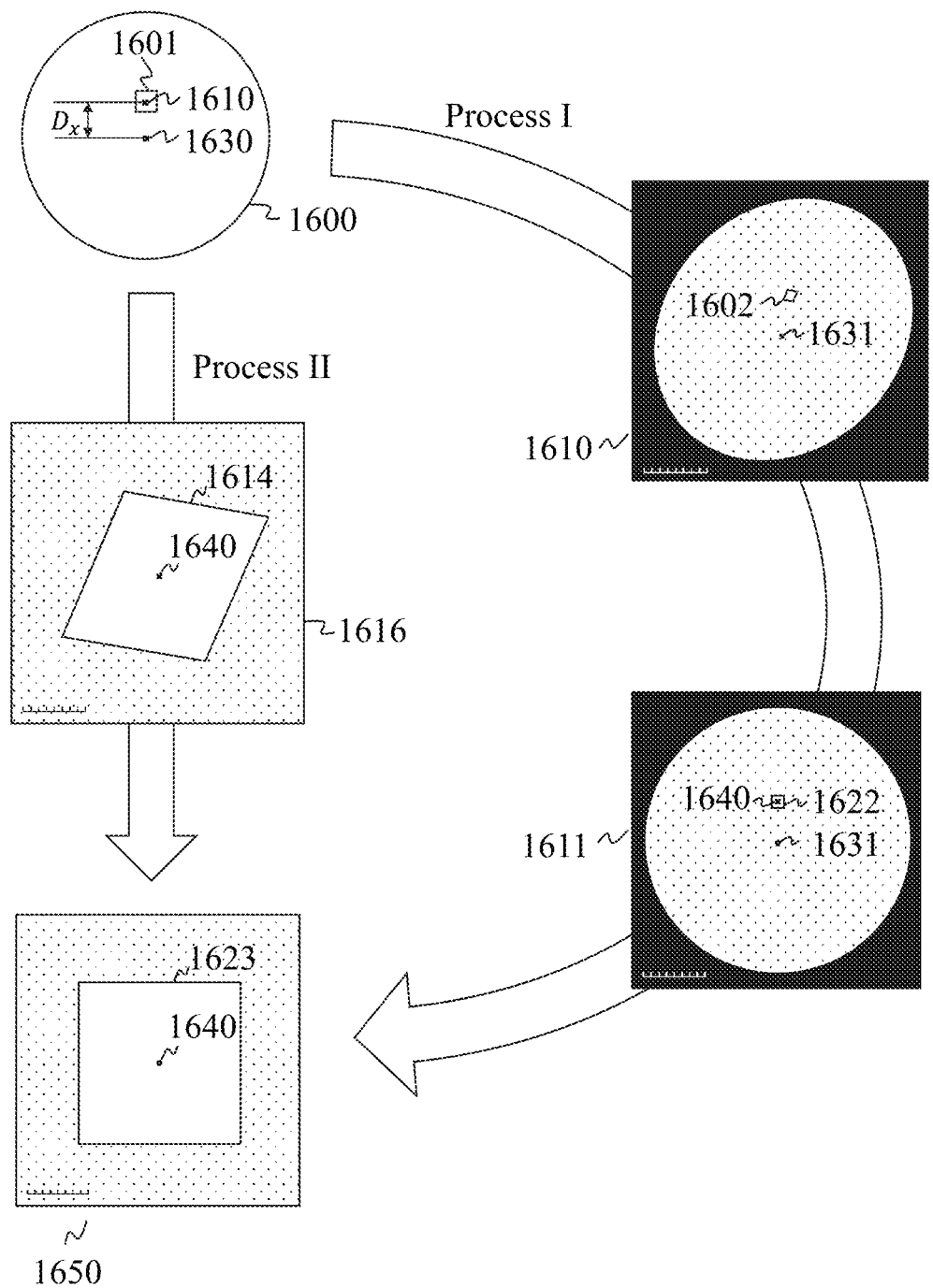
Figure 17:
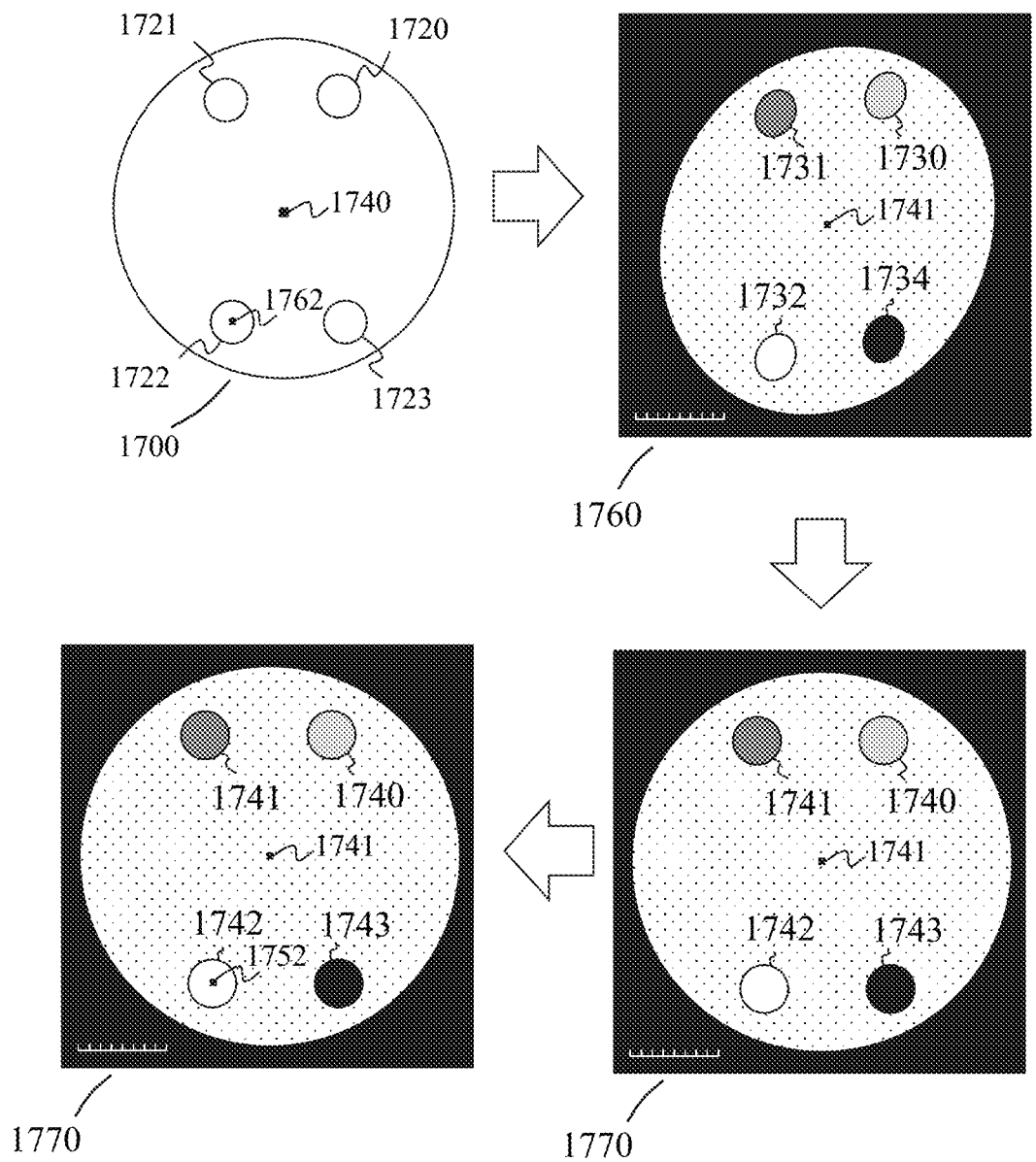
Figure 20:
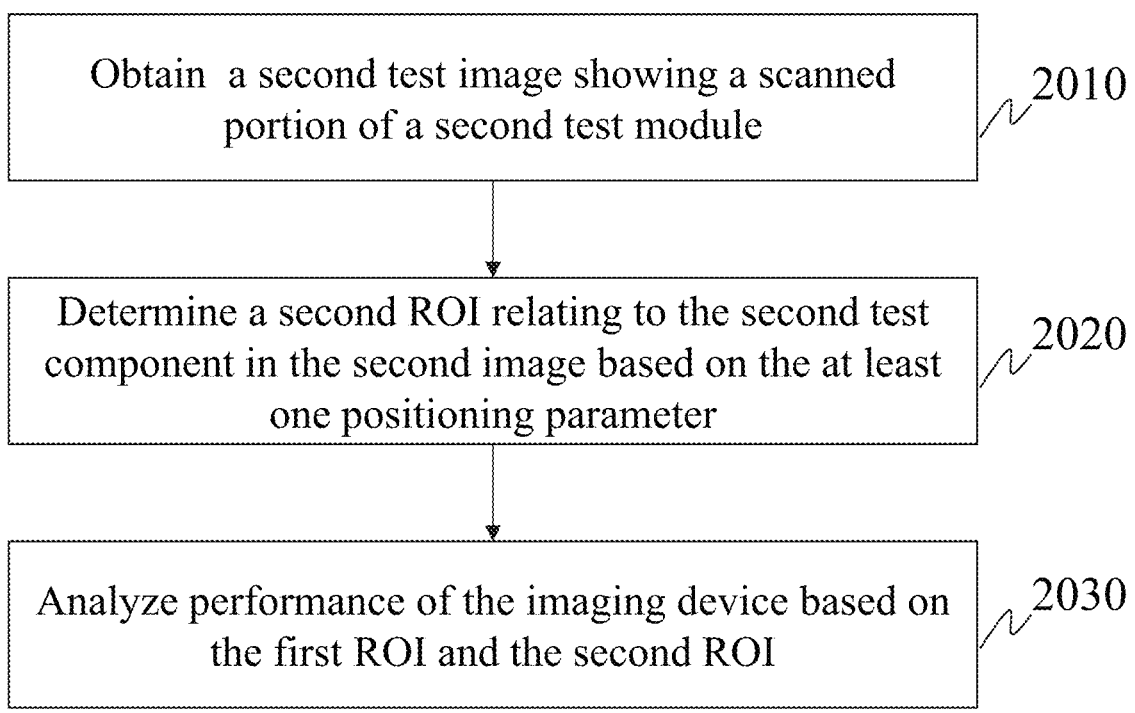
Figure 22:
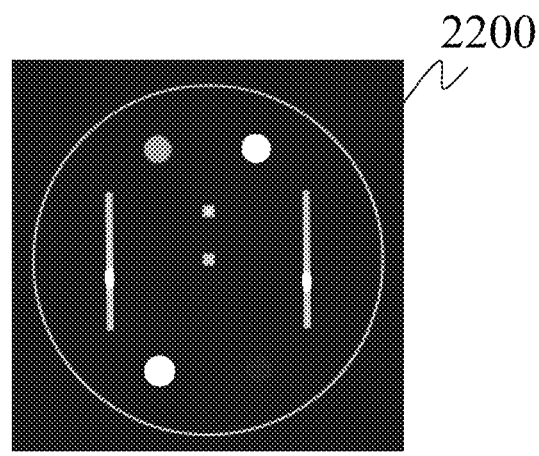
Figure 23:
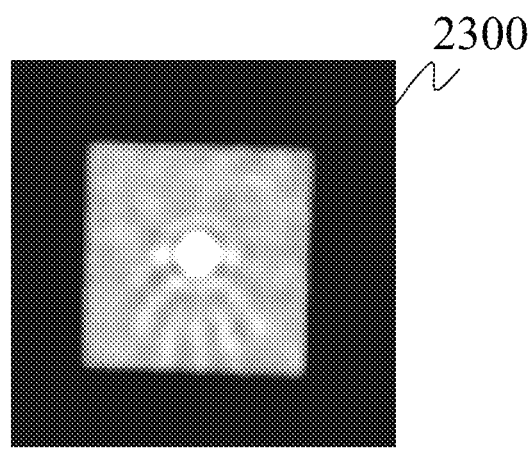
Figure 24:
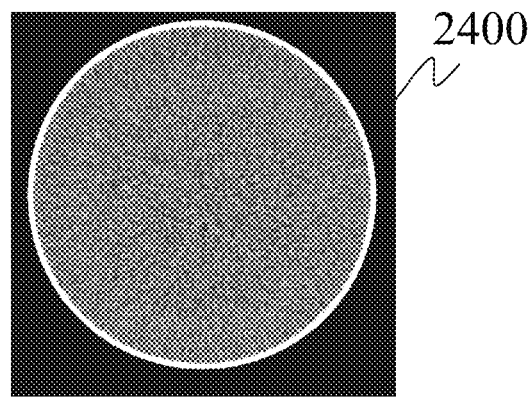

FIGS. 6-A and 6-B are schematic diagrams illustrating exemplary phantoms on a scanner according to some embodiments of the present disclosure;

FIG. 7-A is a schematic diagram illustrating a cross-sectional view of an exemplary phantom according to some embodiments of the present disclosure;

FIG. 7-B is a schematic diagram illustrating a perspective view of a scanned part of the phantom illustrated in FIG. 7-A according to some embodiments of the present disclosure;

FIG. 7-C is a schematic diagram illustrating an exemplary image of the scanned part of the phantom illustrated in FIG. 7-A according to some embodiments of the present disclosure;

FIG. 8 is a flowchart of an exemplary process for determining an ROI in an image of a phantom according to some embodiments of the present disclosure;

FIG. 9-A is a schematic diagram illustrating an exemplary technique for obtaining one or more positioning parameters according to some embodiments of the present disclosure;

FIG. 9-B is a schematic diagram illustrating exemplary locations of one or more positioning modules of a phantom according to some embodiments of the present disclosure;

FIGS. 10-A and 10-B are schematic diagrams illustrating exemplary reference points in the image according to some embodiments of the present disclosure;

FIGS. 11-A and 11-B are schematic diagrams illustrating exemplary techniques for determining one or more slopes of the phantom relative to the scanner according to some embodiments of the present disclosure;

FIG. 12 is a schematic diagram illustrating an exemplary ROI determining sub-module according to some embodiments of the present disclosure;

FIG. 13 is a flowchart of an exemplary process of determining an ROI in a test image according to some embodiments of the present disclosure;

FIGS. 14-A and 14-B are flowcharts of exemplary processes of generating a first test image based on the image data and the at least one positioning parameter according to some embodiments of the present disclosure;

FIG. 15-A is a flowchart of an exemplary process of generating a first test image based on the image data and at least one positioning parameter according to some embodiments of the present disclosure;

FIG. 15-B is a flowchart of an exemplary process of generating a first preliminary ROI in the first test image according to some embodiments of the present disclosure;

FIGS. 16 and 17 are schematic diagrams illustrating exemplary processes for generating a first test image based on the image data and the at least one positioning parameter according to some embodiments of the present disclosure;

FIGS. 18-A, 18-B and 18-C are schematic diagrams illustrating exemplary errors relating to the determined locating points;

FIGS. 19-A and 19-B are schematic diagrams illustrating exemplary ROIs according to some embodiments of the present disclosure;

FIG. 20 is a flowchart of an exemplary process of determining a second ROI based on the received image data according to some embodiments of the present disclosure;

FIG. 21 is a flowchart of an exemplary process of determining a third ROI based on the received image data according to some embodiments of the present disclosure;

FIGS. 22, 23, and 24 illustrate exemplary images generated according to an embodiment of the present disclosure.

DETAILED DESCRIPTION

The present disclosure is directed to methods and systems for analyzing the imaging performance of an imaging system. A region of interest (ROI) may be determined in the image generated according to the scanning by a scanner of the imaging system of a phantom. In an exemplary embodiment, during the determination of the ROI, a preliminary ROI may be determined based on at least one positioning parameter relating to the positioning manner of the phantom during the scanning. The ROI may be determined according to the preliminary ROI using centroid or image segmentation based technique.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise", "comprises", and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

It will be understood that when a unit, engine, module or block is referred to as being "on", "connected to", or "coupled to", another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure.

Figure 1:
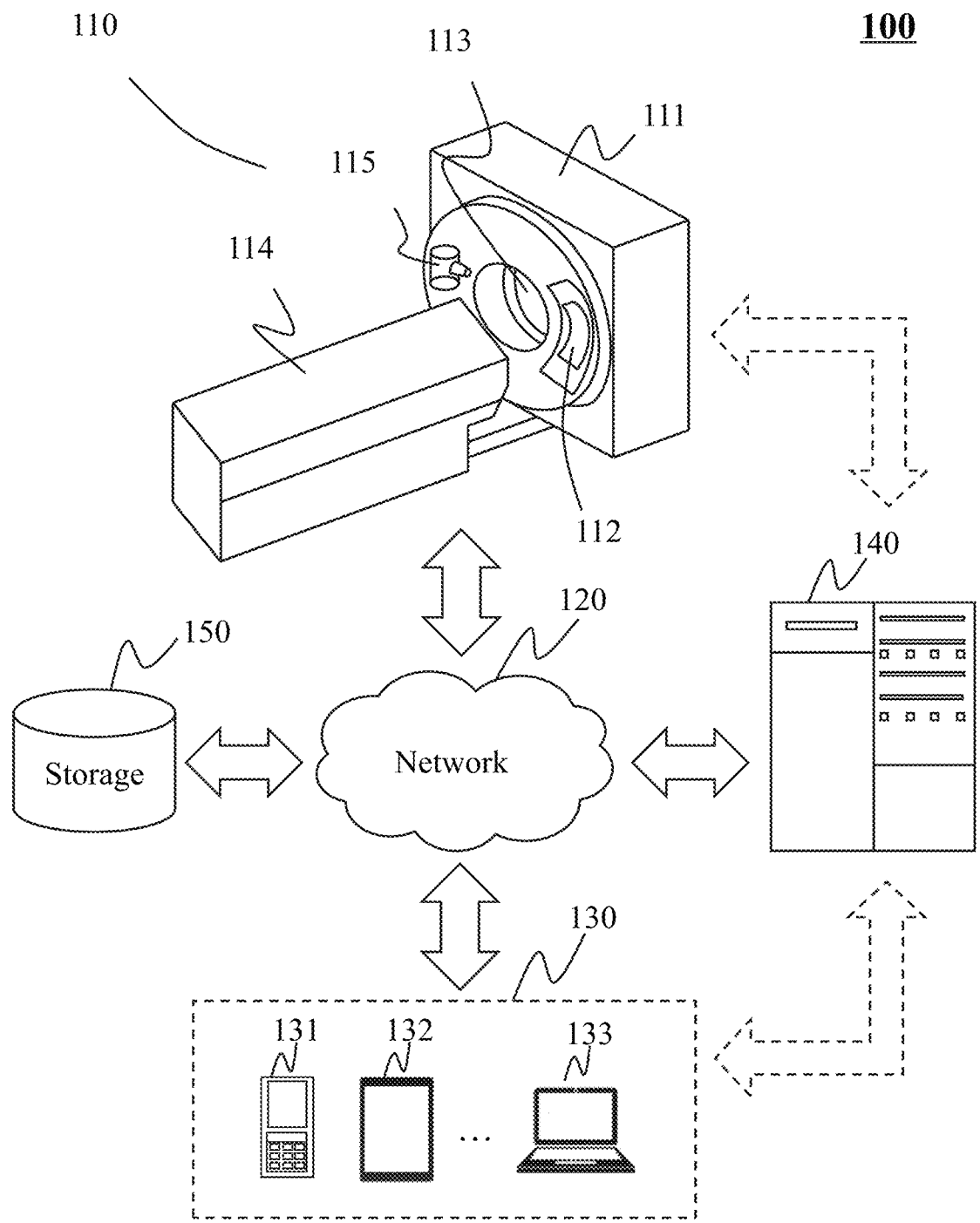
FIG. 1 is a schematic diagram illustrating an exemplary imaging system according to some embodiments of the present disclosure.

FIG. 1 is a schematic diagram illustrating an exemplary imaging system according to some embodiments of the present disclosure. As shown, the imaging system 100 may include a scanner 110, a network 120, one or more terminals 130, a processing engine 140, and a storage 150.

The scanner 110 may include a gantry 111, a detector 112, a detecting region 113, a table 114, and a radioactive scanning source 115. The gantry 111 may support the detector 112 and the radioactive scanning source 115. A subject may be placed on the table 114 for scanning. The subject may be a patient, an experiment subject, a container, an imaging performance analysis subject for the scanner 110 (e.g., a phantom), or the like, or any combination thereof. The radioactive scanning source 115 may emit scanning signals (e.g., radioactive rays, radio waves) to the subject. The detector 112 may detect the responding signals (e.g., gamma photons, X-rays, radio-frequency signal) of the subject to the scanning signals in the detecting region 113 (e.g., a gantry). In some embodiments, the detector 112 may include one or more detector units. The detector unit may be and/or include a single-row detector and/or a multi-rows detector.

The scanner 110 may acquire scan data for generating (or reconstructing) an image via scanning a subject. The imaging system 100 may adopt one or more imaging techniques to acquire the scan data and generate an image based on the scan data. The adopted imaging technique may include but not limited to computed tomography (CT), magnetic resonance imaging (MRI), positron emission tomography (PET), single-photon emission computed tomography (SPECT), etc. The imaging system 100 may also be configured to adopt combined imaging techniques, which may include but not limited to PET-CT, SPECT-CT, PET-MRI, etc. The type of the scanner 110 and the scan data acquired by the scanner 110 may be decided by the type of imaging technique being adopted.

The network 120 may include any suitable network that can facilitate the exchange of information and/or data for the imaging system 100. In some embodiments, one or more components of the imaging system 100 (e.g., the scanner 110, the terminal 130, the processing engine 140, the storage 150) may communicate information and/or data with one or more other components of the imaging system 100 via the network 120. For example, the processing engine 140 may obtain scan data from the scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include, a wearable device, a mobile device, a virtual reality device, an augmented reality device, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the scanner 110, the terminal 130, and/or the storage 150. For example, the processing engine 140 may be configured to process the scan data acquired by the scanner 100 and generate (or reconstruct) corresponding image data. The image data may represent an intensity (e.g., radiodensity, absorbance) distribution in 2D space or 3D space. The image data may be a numerical or digital representation of the interior structure of the subject scanned by the scanner 110. An image (a visual representation of the image data) may be generated based on the image data for providing an interior examination of the scanned subject. In the present disclosure, unless otherwise noted, the term "image" may generally refer to the image data and its visual representation.

The image generated by processing engine 140 may be, for example, a CT image, an MRI image, a PET image, a SPECT image, a PET-CT image, a SPECT-CT image, etc.

The processing engine 140 may be further configured to analyze the imaging performance of the imaging system 100 based on the image data. For example, the scanner 110 may scan a phantom and generate a set of scan data. The processing engine 140 may generate an image based on the set of scan data. The processing engine 140 may analyze the image and determine one or more ROIs in the image. The processing engine 140 may analyze the data of the ROIs for determining one or more parameters related to one or more aspects of the imaging performance of the imaging system 100.

In some embodiments, the processing engine 140 may determine the imaging performance based on one or more positioning parameters of the phantom. The positioning parameters may relate to the positioning manner of the phantom during the scanning performed by the scanner 110. The process for analyzing the imaging performance of the imaging system 100, as well as the techniques for obtaining the positioning parameters, are discussed in detail in the following texts of the present disclosure.

In some embodiments, the processing engine 140 may be further configured to generate a control signal for controlling the scanner 110. For example, the processing engine 140 may control the scanner 110 to scan a subject (e.g., a phantom) in a predetermined manner.

The processing engine 140 may be a computer, a user console, a single server or a server group (centralized or distributed), etc. The processing engine 140 may be local or remote. For example, the processing engine 140 may access information and/or data stored in the scanner 110, the terminal 130, and/or the storage 150 via the network 120. As another example, the processing engine 140 may be directly connected to the scanner 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components illustrated in FIG. 2.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the Imaging system 100 (e.g., the processing engine 140, the terminal 130). One or more components of the imaging system 100 may access the data or instructions stored in the storage 150 via the network 120. In some embodiments, the storage 150 may be directly connected to or communicate with one or more other components of the imaging system 100 (e.g., the processing engine 140, the terminal 130). In some embodiments, the storage 150 may be part of the processing engine 140.

Figure 2:
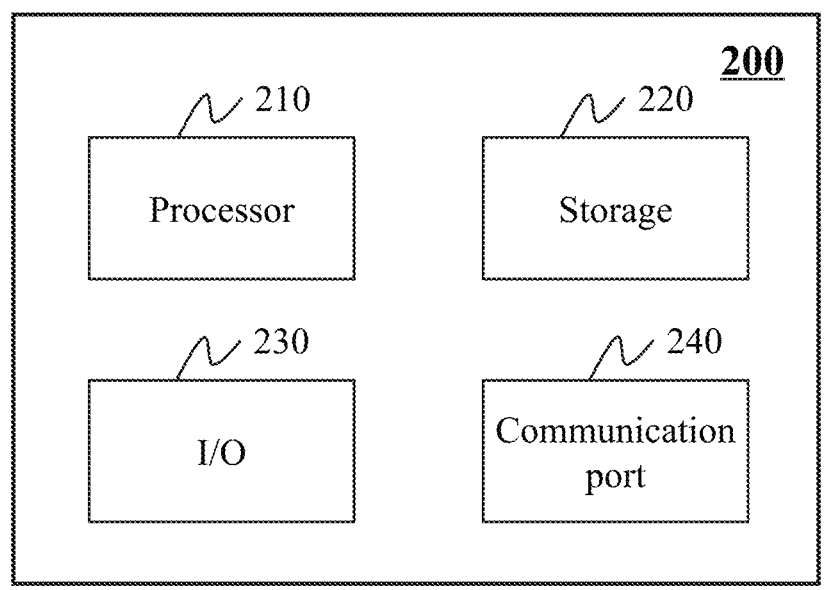
FIG. 2 is a schematic diagram illustrating exemplary components of an exemplary computing device according to some embodiments of the present disclosure.

FIG. 2 is a schematic diagram illustrating exemplary components of an exemplary computing device according to some embodiments of the present disclosure. The processing engine 140 may be implemented on computing device 200. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may be configured to control the scanner 110 to perform a scanning on a subject such as a phantom, generate an image based on the scan data related to the scanning, and analyze the imaging performance of the imaging system 100 based on the image.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus steps and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the scanner 110, the terminal 130, the storage 150, and/or any other component of the imaging system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the scanner 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
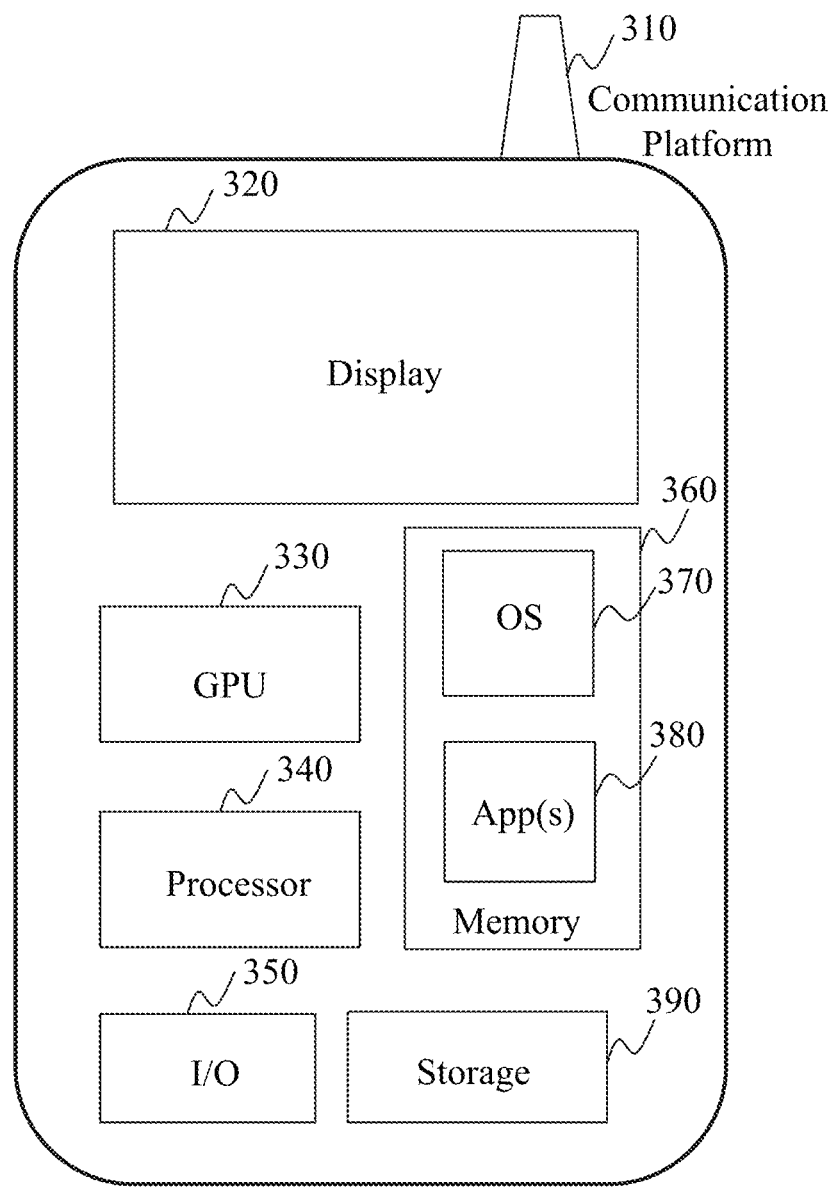
FIG. 3 is a schematic diagram illustrating exemplary components of an exemplary mobile device according to some embodiments of the present disclosure.

FIG. 3 is a schematic diagram illustrating exemplary components of an exemplary mobile device according to some embodiments of the present disclosure. As illustrated in FIG. 3, the mobile device 300 may include a communication platform 310, a display 320, a graphics processing unit (GPU) 330, a processor 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the processor 340. The applications 380 may include a browser or any other suitable mobile apps for receiving and rendering information relating to the image generating process and the imaging performance analyzing process from the processing engine 140. User interactions with the information stream may be achieved via the I/O 350 and provided to the processing engine 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
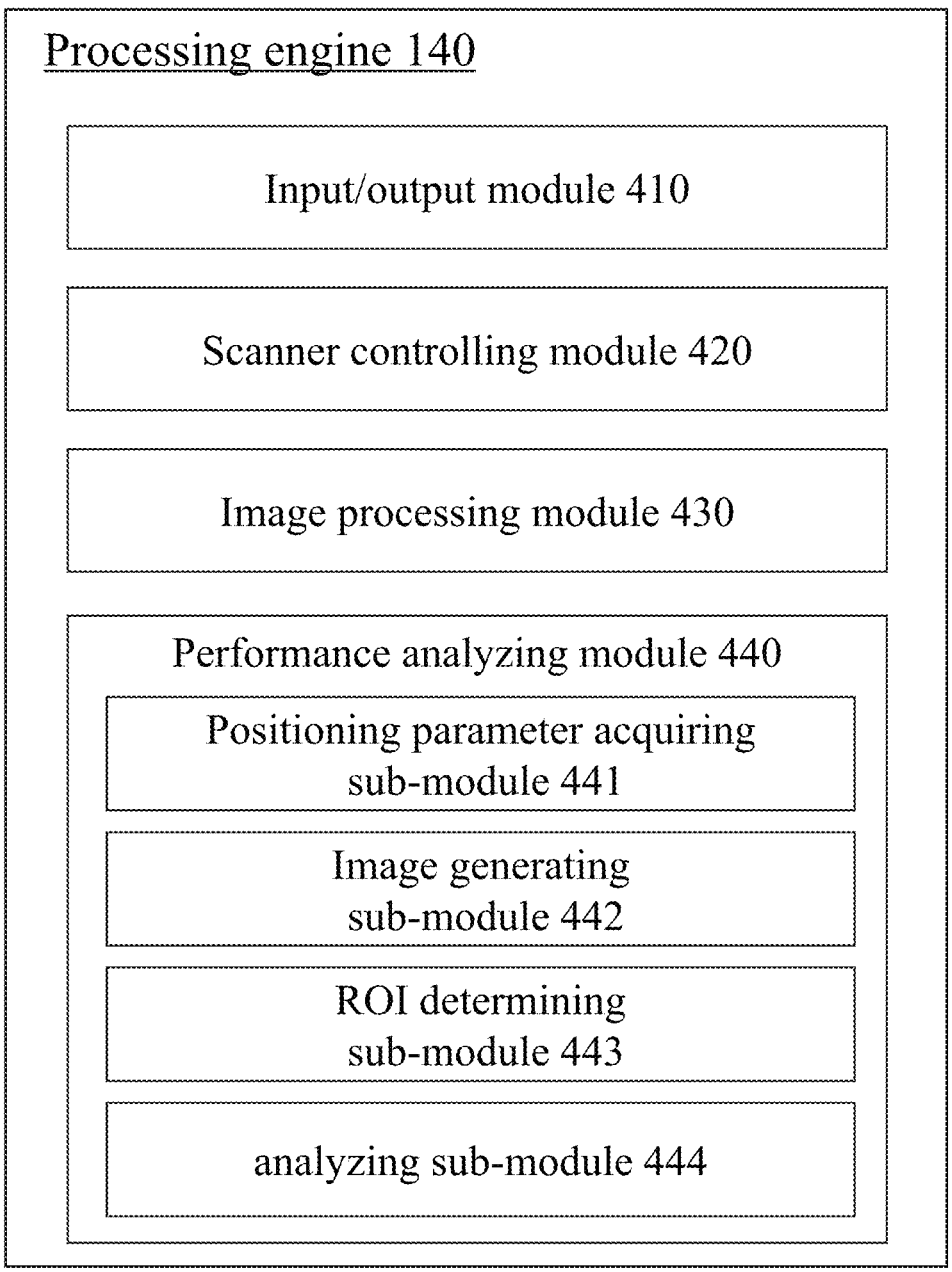
FIG. 4 is a schematic diagram illustrating an exemplary processing engine according to some embodiments of the present disclosure.

FIG. 4 is a schematic diagram illustrating an exemplary processing engine according to some embodiments of the present disclosure. The processing engine 140 may include an input/output module 410, a scanner controlling module 420, an image processing module 430, and a performance analyzing module 440. Other modules may also be included in the processing engine 140.

It may be noticed that the term "module" (and "sub-module," "unit") used in this disclosure generally refers to logic embodied in hardware or firmware, or to a collection of software instructions. The modules described herein may be implemented as software and/or hardware modules and may be stored in any type of non-transitory computer-readable medium or another storage device. In some embodiments, a software module may be compiled and linked into an executable program. It will be appreciated that software modules can be callable from other modules or themselves, and/or can be invoked in response to detected events or interrupts. Software modules configured for execution on computing devices (e.g., the computing device 200, the mobile device 300) can be provided on a computer-readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device (e.g., the storage 220, the memory 360), for execution by the computing device. Software instructions can be embedded in firmware, such as an EPROM. It will be further appreciated that hardware modules can be included of connected logic units, such as gates and flip-flops, and/or can be included of programmable units, such as programmable gate arrays or processors. The modules or computing device functionality described herein are preferably implemented as software modules, but can be represented in hardware or firmware. In general, the modules described in this disclosure refer to logical modules that can be combined with other modules or divided into sub-modules despite their physical organization or storage.

The input/output module 310 may be configured to communicate (e.g., acquire, receive, send) data for the processing engine 140. The data may include data generated by the scanner 110, temporary data generated by the processing engine 140, the control signal generated by the processing engine 140 for controlling the scanner 110, instructions for operating processing engine 140 and/or its modules/units, etc. The data may be communicated with the scanner 110, the terminal 130, the network 120, etc.

The scanner controlling module 420 may be configured to generate a control signal for controlling the scanner 110. The control signal may be generated based on one or more scanning parameters. The scanning parameters may correspond to the type, scanning times, starting time, scanning speed, the scanning region, the scanning condition, etc., of the scanning to be performed or being performed by the scanner 110. The generated control signal may be sent to the scanner 100 to control or guide the scanner 110 performing the corresponding scanning on a subject.

One or more of the scanning parameters may be inputted by a user through the terminal 130, be acquired from the network 120, be acquired from a storing device (e.g., the storage 150, the storage 220, the memory 260), or the like, or a combination thereof. One or more of the scanning parameters may also be determined by one or more modules/units of processing engine 140 (e.g., the performance analyzing module 440).

In some embodiments, one or more of the scanning parameters may be determined based on the data obtained from the scanner 110 by one or more modules/units of the processing engine 140. The data may represent, for example, working state of the scanner 110, working environment of the scanner 110 (e.g., determined by sensors of the scanner 110), data acquired by the scanner 110, data generated by one or more modules installed on the scanner 110, or the like, or a combination thereof. The data obtained from the scanner 110 may be used to generate one or more new scanning parameters or be used to modify one or more predetermined scanning parameters.

The image processing module 430 may be configured to generate (or reconstruct) an image based on the scan data acquired by the scanner 110. Different image reconstruction techniques or data processing techniques may be adopted by the image processing module 430.

In some embodiments, the image processing module 430 may reconstruct one or more slice images based on the acquired data. A slice image may be a 2D cross-sectional image of the scanned subject. The obtained one or more slice images may be directly used for viewing the inside of the scanned subject. Alternatively or additionally, a plurality of slice images may be used for generating a volume image for enhancing the viewing experience.

In some embodiments, the image processing module 430 may directly reconstruct a volume image without the generating a plurality of slice images during the reconstruction process. A cross-sectional part of the volume image, however, may also be referred to as a slice image in the present disclosure.

In some embodiments, the image processing module 430 may generate the image based on one or more image generating parameters. The one or more image generating parameters may include the parameter related to the reconstruction center (e.g., in the form of coordinates, pixel, or voxel), the image quality, the field of view (FOV), the orientation of the image, etc. The one or more image generating parameters may be inputted by a user through terminal 130, or be generated by one or more modules or sub-modules of processing engine 140 (e.g., the image generating sub-module 442).

The generated slice image(s) and/or volume image may be used for disease diagnosing, security inspection, scientific research. In some embodiments, the generated slice image(s) and/or volume image (e.g., of a phantom) may be used for analyzing the imaging performance of the imaging system 100. In the present disclosure, analyzing the imaging performance may generally include obtaining one or more imaging parameters. An imaging parameter may be a mathematical description of the imaging capability of a scanner, a parameter for an imaging technique adopted by the scanner, or a parameter for an image reconstruction technique adopted by the processing engine 140, or the like, or a combination thereof. An imaging parameter may relate to slice thickness, slice sensitivity profile (SSP), linearity, modulation transfer function (MTF), pixel size, spatial uniformity, low contrast, a noise value, or the like, or any combination thereof.

The performance analyzing module 440 may be configured to analyze the imaging performance of the imaging system 100. The performance analyzing module 440 may analyze the imaging performance based on image data relating to a scanning, by the scanner 110, of at least part of a phantom. In the present disclosure, the term "phantom" generally relates to an object that is scanned or imaged by a scanner (e.g., the scanner 110) to evaluate, analyze, and/or tune the imaging performance of the imaging system 100.

Figure 5:
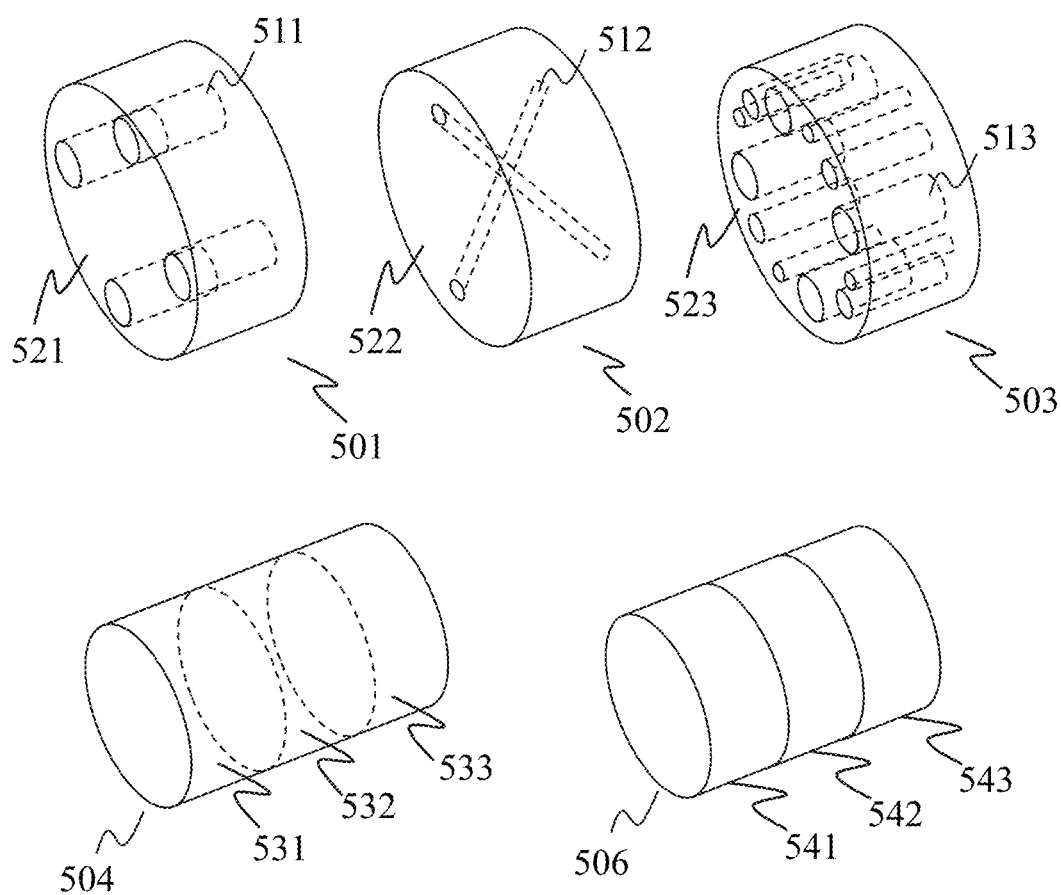
FIG. 5 is a schematic diagram illustrating exemplary phantoms according to some embodiments of the present disclosure.

FIG. 5 is a schematic diagram illustrating exemplary phantoms according to some embodiments of the present disclosure. A phantom (e.g., the phantom 501, 502 or 503) may include a body (e.g., the body 521, 522 or 523.) and one or more test component (e.g., the test components 511, 512, and 513). The test component(s) may be used for the imaging performance analysis.

The test component may be used for analyzing imaging performance of the imaging system 100. The material (e.g., Teflon, acrylic, Delrin, polystyrene, low-density polyethylene (LDPE), air, water, metal), shape (e.g., sphere, cube, rod, wire, ramp, columns or disks with various cross-sectional shapes), size, and positioning pattern (e.g., vertical, horizontal, tilted) of a test component may be decided based on the specific imaging parameter(s) to analyze. It may take one test component or a group of test components to analyze one aspect of the imaging performance. For example, it may take one test component to analyze the MTF of a scanner. As another example, it may take a set of (e.g., 4) test components to analyze the linearity of a scanner. As a further example, it may require one test component to analyze the SSP of a scanner, but multiple test components may be used to analyze the SPP together for eliminating or reducing possible errors. Test component(s) for analyzing one aspect of the imaging performance may be grouped as a test module in the present disclosure. A phantom may include only one test module or multiple test modules.

The body of the phantom may provide mechanical support to the test component(s). A test component may be embedded into the body or be packaged by the body. Compared to the test component, the body may have none, negligible, or reduced response to the scanning signal emitted by the scanner being analyzed. Thus the body may be less notable in the generated image of the phantom than the test component. The body may be a disk-like or column-like object. The cross-section of the body may be circle, square, rectangle, oval, or any other proper shape. The body may be solid or hollow. In some embodiments, the body may also include other components or modules. For example, the body may include a housing for protective purpose and/or for fixing the phantom onto the table 114. As another example, the body may include one or more connectors to connect different parts of the phantom.

A phantom may include only one section (e.g., the phantom 501, 502, or 503) or multiple sections (e.g., the phantom 540 or 506; the test components are hidden for clarity). These sections may be separable (e.g., the sections 541, 542 and 543), or inseparable (e.g., the sections 531, 532 and 533). The separable sections may be viewed as multiple bodies, and inseparable section may be viewed as different part of one body. A phantom with multiple bodies may include a housing for holding the bodies. Alternatively or additionally, the bodies may include connectors for connecting with each other.

Different sections of phantom may include different test modules. For example, in the phantom 504, the section 531 may have a similar structure to the phantom 511, the section 532 may have a similar structure to the phantom 512, and the section 533 may have a similar structure to the phantom 503. For analyzing one or more aspects of imaging performance of the imaging system 100, the corresponding section of the phantom may be scanned and imaged. For a phantom with multiple separable sections (bodies), bodies needed to be scanned may be connected and then scanned by the scanner. For a phantom (or a body of a phantom) with multiple inseparable sections, the unrelated sections may be omitted during the scanning.

For analyzing the imaging performance of an imaging system using a specific imaging technology or for a specific application, a specific type of phantom may be used. For example, a phantom for a radiography scanner may include test component(s) with similar x-ray absorbing properties to the subject of the radiography scanner. A phantom for an ultrasonography scanner may include test component(s) with similar rheological and ultrasound scattering properties to the subject of the ultrasonography scanner. As another example, a phantom for a medical used radiography scanner may include test component(s) with similar x-ray absorbing properties to tissues (e.g., bones, muscles, fats) of human body, while a phantom for a security-inspectional used radiography scanner may include test component(s) with similar x-ray absorbing properties to the material of the scanning target (e.g., liquid, metal). The test component(s) may be made of the material of the scanning target to fulfill the purpose.

It may be noticed that the drawings of phantom illustrated in FIG. 5 and the related description are only for demonstration purposes and are not intended to limit the appearance, number, type, structure, material, function, or usage of the phantom, the body or the test component. The imaging performance analysis method described in the present disclosure may be used with phantoms designed for different kinds of imaging systems. For demonstration purposes, and also for brevity, the following text of the present disclosure may mainly focus on the imaging performance analysis of a CT imaging system for medical use. However, this is not intended to limit the imaging technique or the application of the imaging system 100.

Referring back to FIG. 4, the performance analyzing module 440 may include a positioning parameter acquiring sub-module 441, an image generating sub-module 442, an ROI determining sub-module 443, and an analyzing sub-module 444. One or more additional sub-modules may also be included in the performance analyzing module.

The positioning parameters acquiring sub-module 441 may be configured to acquire at least one positioning parameter, which may indicate the positioning manner of the phantom during the scanning. In the present disclosure, the positioning manner of the phantom generally refers to the location and the angle of the phantom relative to the scanner during the scanning. A positioning parameter may relate to, for example, a location (e.g., in the form of coordinates) of a physical point or a module of the phantom relative to the scanner, the axial direction (e.g., in the form of one or more slopes) of the phantom relative to the scanner, or the like, or any combination thereof.

FIGS. 6-A and 6-B are schematic diagrams illustrating exemplary phantoms on a scanner according to some embodiments of the present disclosure. A coordinate system (e.g., a 3D Cartesian coordinate system as shown in FIGS. 6-A and 6-B including an x axis, a y axis and a z axis) may be adopted by the imaging system 110 for indicating the region scanned (scan region or scan space) by the scanner 110 during the scanning and the image space of the corresponding image generated based on the scanning. The scan region may be a region that the scanner 110 scans during a scanning. The scan region may be relative to a component of the scanner 110 (e.g., the gantry 111, the table 114). For example, the scan region may be a region above the table 114 which may include the target scan part of a subject to be scanned.

The exemplary coordinate system shown in FIGS. 6-A and 6-B, which is used throughout this disclosure, is described as following. The direction of the z axis may be the direction that the scanning being performed by the scanner 110. The direction of the z axis may be set as horizontally pointing from the table 114 to the detecting region 113. The direction of the y axis may be set as pointing horizontally from the left side to the right side of the table 114 (facing the direction of z axis). The direction of the x axis is vertically from the table 114 to the above. The x axis, y axis and z axis may be set as perpendicular to one another. The x axis and the y axis may determine the plane XY, the x axis and the z axis may determine the plane XZ, the y axis and the z axis may determine the plane YZ. The plane XY may be generally known as a transverse or axial plane. The plane XZ may be generally known as a median or sagittal plane. The plane YZ may be generally known as a frontal or coronal plane.

It may be noticed that the imaging performance analysis method described in the present disclosure may be used for an imaging system using other kinds of coordinate systems (e.g., a polar coordinate system, a cylindrical or spherical coordinate system, a similar coordinate system) in practical use.

In some embodiments, a phantom (e.g., the phantom 600) may be installed on the table 114 through a fixing structure 610 (e.g., one or more brackets). The fixing structure may be used to attach the phantom to a predetermined location or an arbitrary location on the table 114, and prevent the movement of the phantom 600 during the scanning. The fixing structure 610 may be connected to the body or the housing (if any) of the phantom 600. The phantom 600 may be placed at least partially protruding from the table 114 in the direction of the scanning (as shown in FIG. 6-A) or right above the table.

In some embodiments, a phantom (e.g., the phantom 601) may be placed on the table 114 without any fixing structure. The phantom 601 may be placed at a predetermined location or an arbitrary location on the table 114.

The scanning may be performed in the direction of the z axis by the scanner 110. The phantom may be moved to the detecting region 113 by the table 114, or the detecting region 113 may be moved to the phantom by the gantry 111. In some embodiments, the phantom may be placed on or attached to the table 114 in a manner that the central axis of the phantom pointing right to the direction of the z axis for analyzing the imaging performance. In some cases, however, the phantom may not be placed so precisely that the central axis of the phantom may be biased from the direction of the z axis to various degree (e.g., due to the manual step errors and/or systematic errors), which may cause the tilt of the phantom in the obtained image data and the image generated therefrom. Alternatively or additionally, the phantom may not be placed exactly at the required placing location. For example, the phantom may be placed deviating (e.g., due to the manual step errors and/or systematic errors) from the target placing location in the direction of the x axis, the y axis and/or the z axis, which may cause the translation of the phantom to the corresponding direction in the obtained image data and the image generated therefrom. In these situations, the translation and/or the tilt of the phantom in the obtained image data may cause decreased accuracy of imaging performance analysis. Also, for arbitrarily placed phantoms, additional information relating to their positioning manner during the scanning may be required for imaging performance analysis.

Referring back to FIG. 4, to reduce the influence of the translation and/or the tilt of the phantom in the obtained image or to provide the information relating to the positioning manner of the placed phantom, the positioning parameter acquiring sub-module 441 may determine the positioning manner of the phantom during the scanning. The positioning parameter acquiring sub-module 441 may acquire a positioning parameter indicative of the positioning manner of the phantom during the scanning. The positioning parameter may include, for example, the slops (or tilt) of the phantom (or the axis of the phantom) relative to a first direction, a second direction and/or a third direction (e.g., the directions of the z axis, the y axis, and the x axis, or the normal direction of the plane XY, the plane XZ, and the plane YZ). The positioning parameter may also include one or more reference points in the image of the phantom (e.g., coordinates, a pixel, a voxel). A reference point (e.g., the point 792 illustrated in FIG. 7) may correspond to a physical point (e.g., the point 791 illustrated in FIG. 7) of the phantom.

The positioning parameter acquiring sub-module 441 may acquire the positioning parameter from a user via the I/O 230 or the I/O 350, from a storage device (e.g., the storage 150, the storage 220, the storage 390). In some embodiments, the positioning parameter acquiring sub-module 441 may obtain one or more positioning parameters during the scanning in real time.

The image generating sub-module 442 may be configured to generate an image based on the received scan data. The generated image may be one or more slice images and/or a volume image of the phantom. The generated image may be used for the determination of ROI. The image generating sub-module 442 may generate the image of the phantom. Alternatively or additionally, the image generating sub-module 442 may output related image generating parameters to the image processing module 430. In some embodiments, the image generating sub-module 442 may generate the image based on the determined positioning parameter and the received scan data.

FIG. 7-A is a schematic diagram illustrating a cross-sectional view of an exemplary phantom according to some embodiments of the present disclosure. FIG. 7-B is a schematic diagram illustrating a perspective view of a scanned part of the phantom illustrated in FIG. 7-A according to some embodiments of the present disclosure. FIG. 7-C is a schematic diagram illustrating an exemplary image of the scanned part of the phantom illustrated in FIG. 7-A according to some embodiments of the present disclosure. Phantom 700 may include a plurality of test components (e.g., the test components 711 to 717). The phantom 700 may be a disk or cylinder-shaped object with an axis 790.

The phantom 700 may include a plurality of sections (separable or inseparable), while FIG. 7-A demonstrates the cross-sectional view of only one of the sections, i.e., section 701. The section 701 may include multiple test components. The test components may be grouped into one or more test modules. A test module may include one or more test components for analyzing one aspect of the imaging performance of the imaging system 100. For example, the section 700 may include a test module (including CT number linearity related test components 713 to 716) for analyzing CT number linearity, a test module for analyzing the SSP (including the SSP related test components 711 and 712) and a test module for analyzing the MTF (including the MTF related test component 717). Section 701 may further include an additional module 718. The module 718 may be a test module with one test component or a module for other use. For example, the module 718 may be used to locate the section 701 in the phantom 700 to perform selective scanning, to identify the image data corresponding to the section 701 in the image data corresponding to the phantom 700, to determine one or more ROIs in an image of the section 701, or the like, or a combination thereof.

FIG. 7-B illustrates a perspective view of a scanned part (the scanned part 702) of the phantom 700 (or the section 701). The scanned part 702 may be the part of the phantom 700 (or the section 701) scanned by the scanner 110 for imaging performance analysis. During the scanning, the phantom 700 may be placed on the table 114 in a manner that the axis 790 is parallel with the z axis. The scanning may be performed along the z axis and a plurality of slice image (e.g., the image 770) may be generated based on the scanning. Each slice image may correspond to a cross-section of the phantom 700 (e.g., the cross-sections 751, 752, 753 and 754) along the z axis. The cross-sectional view illustrated in FIG. 7-A may correspond to the cross-section 751.

The test components of the phantom 700 may have various shapes, sizes, and may locate at different locations in the phantom 700. The scanned part 702 may contain at least a part of a test component (or parts of multiple test components of a test module) relating to an imaging parameter (or an imaging parameter set) to be analyzed. The cross-sections 751 to 754 may each include a cross-section of the related test component (or cross-sections of the related test components). The corresponding slice images may each include an image region representing the related test component (or image regions representing the related test components).

The image 770 may be one of the generated slice images. The image 770 may correspond to, for example, the cross-section 751. The image 770 may include image regions (e.g., the image regions 771 to 778) corresponding to the test components and modules included in the scanned part 702. One or more ROIs (e.g., the ROIs 762 to 767) may be determined within the image regions.

Generally, an ROI is a selected subset of samples within a dataset identified for a particular purpose. An ROI may be the image region corresponding to a test component in an image of the phantom for imaging performance analysis. An ROI may substantially (e.g., the ROIs 761, 762) or partially (e.g., the ROIs 763 to 767) cover the image region representing a test component. An ROI and the corresponding image region may have similar (e.g., the ROIs 761 to 766) or different (e.g., the ROI 767) shapes.

For a slice image, an ROI may be a 2D image region. For a volume image, an ROI may be 3D image region. An image may be a video. For a video (2D or 3D), an ROI may be a set of the related image regions (with uniform or variable shapes and/or sizes) in a series of frames of the video.

The ROI determining sub-module 443 may use the image data of an ROI for imaging performance analysis. The ROI determining sub-module 443 may perform an ROI determination for the image of the phantom (e.g., the image 770). The ROI determining sub-module 443 may determine one or more ROIs in the image for analyzing one aspect of the imaging performance of the imaging system 100. For example, for analyzing CT number linearity, The ROIs 763-766 (corresponding to the CT number linearity related test components 713 to 716) may be determined in the image 770; for analyzing MTF, The ROI 767 (corresponding to the MTF related test component 717) may be determined in the image 770; for analyzing SSP, the ROI 761 and/or the ROI 762 (corresponding to the SSP related test component 711 and/or 712) may be determined in the image 770.

It may be noticed that the above description of the phantoms, ROIs, test components in connection with FIGS. 7-A to 7-C are only for illustration purposes and are not intended to limit the scope of the present disclosure. Modifies may be made to the above description. For example, the phantom 700 may only contain one section; the phantom 700, the section 701, and/or the scanned part 702 may only contain one test component; the scanned part 702 may be the whole phantom 700; the test components 711 to 717 and the module 718 may occupy other locations of phantom 700; one or more test components and/or modules may be added or removed from phantom 700; the shape and/or size of the phantom 700 and test components may be changed, etc.

Referring back to FIG. 4, the ROI determining sub-module 443 may be configured to determine one or more ROIs in the image of phantom generated by the image generating sub-module 442 or the image processing module 430 automatically or semi-automatically. The ROI determining sub-module 443 may determine one or more ROIs based on one or more positioning parameters obtained by the positioning parameter acquiring sub-module 441.

The determination of an ROI may be based on the determination of the location of image region representing the corresponding test components in the image of the phantom in the present disclosure. In some embodiments, during the scanning, the phantom may be fixed or placed at a predetermined location on the table 144 with a predetermined positioning manner (e.g., the axis of the phantom may be parallel with the z axis). According to the structural information of the phantom, the ROI determining sub-module 443 may determine the location of a target test component in the scan region. The ROI determining sub-module 443 may determine the location of image region representing the target test component in the image based on the location of the targeted test component in the scan region. An ROI may be determined by the ROI determining sub-module 443 based on the location of image region of the target test component.

The structural information may be provided with the phantom (e.g., in a specification or a computer-readable media) or be included in the software, update patch, or database provided with the phantom. The structural information may also be downloadable content acquired or downloaded by the terminal 130 or the processing engine 140 via, for example, the network 120, given the type or the serial number of the phantom. The structural information may also be acquired (e.g., by measuring and registering) directly from the phantom. The obtained structural information may be stored in a storage device (e.g., the storage 150, the storage 220, the storage 390).

The structural information may include parameters indicating the location and related information (e.g., serial number or name, function, shape, size) of the components (e.g., test components) and modules (e.g., test modules) of the phantom. The location of a component/module described herein refers to the component's absolute location or relative location relative to a physical point in the phantom. This physical point may be referred to as a base point. For example, structural information may include parameters representing the direction and the distance of the target test component from the base point in the phantom.

In some embodiments, the base point may be a central point (e.g., the point 791) of the phantom. A central point described herein may refer to a point locating substantially at the axis (e.g., the axis 790) of an object (e.g., the phantom 700). For determining one or more ROIs in a slice image (e.g., the image 770), the base point may refer to the central point of the phantom locating at the corresponding cross-section (e.g., the cross-section 751) cutting through the corresponding test component(s). For determining one or more ROIs in a volume image, the base point may be the point locating at the center of the corresponding volume of the phantom or a central point locating at an arbitrary cross-section cutting through the corresponding test component(s). According to the types and/or shapes of the phantoms, different base point or multiple base points may be used for obtaining the location(s) of the component(s)/module(s) in the phantom.

In some embodiments, the base point may be a module (e.g., the module 718) or the central point of the module. The module may or may not locate at the axis of the phantom.

In some embodiments, for determining the location of the image region representing the target test component in the image of the phantom, the ROI determining sub-module 443 may obtain a reference point (e.g., the point 792) in the image corresponding to the base point (e.g., the point 791) in the phantom. The location of the image region corresponding to a target test component may then be determined by the ROI determining sub-module 443 based on, for example, the obtained reference point and the structural information indicating the location of the target test component relative to the base point in the phantom. The reference point may be input by a user through the terminal 130 or be determined by the positioning parameter acquiring sub-module 443 as a positioning parameter.

In some embodiments, the location of image region representing the target test component in the image of phantom may be determined in the form of a point (e.g., coordinates, a pixel, a voxel). This determined point may be referred herein as a locating point in the image. A locating point in the image may correspond to a physical point of the corresponding test component. This physical point of the corresponding test component may be referred herein as a target point. The locations of the test components described by the structural information may refer to the locations of target points of the corresponding test components relative to a base point. In some embodiments, a target point may be a central point of a test component.

In some embodiments, the ROI determining sub-module 443 may determine an ROI based on a locating point.

In some embodiments, the phantom may not be fixed or placed precisely at the predetermined location, or the phantom may be placed freely on the table 114 without any predetermined location. The ROI determining sub-module 443 may determine the location of the target test component in the scan region and/or the locating point of the target test component in the image of phantom based on the one or more positioning parameters obtained by the positioning parameter acquiring sub-module 441. The one or more positioning parameters may be used for, for example, finding a reference point in the image, determining a locating point corresponding to a target test component in the image, setting one or more image reconstruction parameters (e.g., setting the reconstruction center of the image for eliminating or reducing the translation of image), translating and/or rotating the image (e.g. for eliminating or reducing the translation and/or tilt of image), processing the image data (e.g., for digitally eliminating or reducing the translation and/or tilt of the image), or the like, or any combination thereof.

In some embodiments, due to error, imprecision and/or misoperation issues relating to the manufacturing of the phantom, the measuring of the related parameters, the installing of the phantom, the registering of the structural information, the inputting of structural information into the processing engine 140, or the like, or a combination thereof, the structural information may not be correct or precise enough for an accurate or precise ROI determination. As another aspect, the determined reference point may not be precisely at its supposed location in the image due to error, misoperation, and/or imprecision issues relating to the positioning parameter obtaining process. As a result, the determined locating point of the target test components in the image of the phantom may be off from the supposed location. Errors related to the determined locating points are discussed below in connection with FIGS. 18-A to 18-C. The incorrectly determined locating point may cause an inaccurate determination of the corresponding ROI, which may, in turn, affect the accuracy and precision of the imaging performance analyzing the result.

For reducing or eliminating the potential errors of the determined locating point, the ROI determining sub-module 443 may first determine a preliminary ROI based on the determined locating point. The preliminary ROI may be an image region including the ROI. The ROI determining sub-module 443 may then determine the ROI with the preliminary ROI by centroid based technique, image segmentation, and/or other possible techniques. For example, in an image view, the preliminary ROI may have a center (precisely or approximately) at the locating point and may have predetermined shape (e.g., circle, squire) and/or size; in a data view, the preliminary ROI may be the image data corresponding to its image form. In the present disclosure, only the image view of the ROI and preliminary ROI may be described for concise and demonstration purposes.

The analyzing sub-module 444 may analyze the imaging performance of the imaging system 100 based on the one or more ROIs determined by the ROI determining sub-module 443. The image data related to the determined ROI(s) may be used for imaging performance analysis. A processing result of the image data of an ROI may be output by the analyzing sub-module 444 as an analyzing parameter corresponding to this ROI. The processing result may be a median of the grey scales of the pixels of the ROI, an integral of the grey scales of the pixels of the ROI, a spatial distribution function of the grey scales of the pixels of the ROI, a time variation function related to the grey scales of the pixels of the ROI, or the like, or any combination thereof. One or more analyzing parameters may be used to determine an imaging parameter or a group of related imaging parameters, which may describe one or more aspects of the imaging performance of the imaging system 100 (e.g., slice thickness, slice sensitivity profile (SSP), linearity, modulation transfer function (MTF), pixel size, spatial uniformity, low contrast, noise value, or the like, or any combination thereof). According to the analyzing result, one or more devices/modules/units of the imaging system 100 may be adjusted, calibrated, reset, updated, and/or replaced for enhancing the overall imaging performance.

In some embodiments, the analyzing sub-module 444 may use a plurality of slice images corresponding to different cross-sections (e.g., the cross-sections 751 to 754) for imaging performance analyzing. The plurality of slice images may include the image regions representing the same test component (or the same plurality of test components). The ROIs corresponding to the same test component(s) may be used together for determining the imaging performance of the imaging system 100. For example, the analyzing sub-module 444 may use the image data of the ROIs corresponding to the same test component to generate one processing result, which may then be used by the analyzing sub-module 444 for determining an imaging parameter or a group of related imaging parameters. Alternatively or additionally, the analyzing sub-module 444 may determine an imaging parameter or a group of imaging parameters for each slice image. The obtained imaging parameters or groups of related imaging parameters may be processed (e.g., averaged, sampled) by the analyzing sub-module 444 for determining a final output.

It may be noticed that the above description about the processing engine 140 is only for illustration purposes, and is not intended to limit the present disclosure. It is understandable that, after learning the major concept and the mechanism of the present disclosure, a person of ordinary skill in the art may alter the processing engine 140 in an uncreative manner. The alteration may include combining and/or splitting certain modules/units, adding or removing optional modules/units, or the like, or a combination thereof. For example, the processing engine 140 may be configured for analyzing imaging performance of a second imaging system, and the scanner controlling module 420 and/or the image processing module 430 may belong to the second imaging system and not included in the processing engine 140. Alternatively or additionally, the processing engine 140 may further include one or more modules/units for, for example, image segmentation, image recognition, image rendering, image enhancing, pathologic analysis, etc. The legal protection scope will be defined by the description of claims.

FIG. 8 is a flowchart of an exemplary process for determining an ROI in an image of a phantom according to some embodiments of the present disclosure. One or more steps of process 800 may be performed by one or more modules and/or sub-modules of processing engine 140. In some embodiments, the one or more modules and/or sub-modules may be implemented by the processor 210 or the processor 340.

In 810, the performance analyzing module 440 may receive image data relating to a scanning of the first part of a phantom including at least part of a first test component. The first test component may be a target test component or one of the test components belonging to a target test module (a first test module) relating to an aspect (a first aspect) of the imaging performance to be analyzed (e.g., MTF, SSP). The first test module may be a single-component module or a multi-component module. The other test component(s) included in a multiple-components first test module may also be referred to as first test component(s). One or more corresponding ROIs (first ROIs) may be determined for one or more first test components through process 800.

The first part of the phantom may refer to the part of the phantom including at least part of the first test component. The first part of the phantom may be a section (e.g., the sections 531 to 533, the sections 541 to 543) of the phantom, or a part of a section (e.g., the part of phantom between cross-section 751 and 753) which includes at least part of the first test component. The first part of the phantom may include a plurality of first test components or a portion of each. Alternatively, the first part of the phantom may be the whole phantom. In some embodiments, besides the first test module, the first part of the phantom may include one or more other test modules (e.g., a second test module) including one or more test components (e.g., one or more second test components).

In some embodiments, the phantom may be scanned selectively by the scanner 110, and the image data received by the performance analyzing module 440 may relate to the test component(s) included in the scanned part (e.g., the first part) of the phantom. The selective scanning process may include the determination of the location of the first part relative to the scanner 110.

In some embodiments, the determination of the location may be made by a user. For example, the user may input parameters relating to the location of the first part of the phantom relative to the scanner 110. The scanner controlling module 420 may generate control signals based on the parameters inputted by the user and transmit the control signal to the scanner 110 to perform the selective scanning. Alternatively or additionally, the determination of the location may be made by the performance analyzing module 440. In some embodiments, the performance analyzing module 440 may determine the location of the first part in the phantom based on the aspect(s) of imaging performance to be analyzed and the structural information of the phantom, and then determine the location of the first part relative to the scanner 110 based on one or more positioning parameter relating to the positioning manner of the phantom. The location of the first part relative to the scanner 110 may then be transmitted to the scanner controlling module 420 to generate controlling signals for performing the selective scanning. The one or more positioning parameter may be obtained by the positioning parameter acquiring sub-module 441 in step 820, which may be performed prior to the step 810 in some embodiments.

In some embodiments, the determined location of the first part in the phantom may be transmitted to the scanner controlling module 420 to generate controlling signals, which may be transmitted to the scanner 110 for performing the selective scanning. The scanner 110 may be installed with one or more detectors (e.g., the detector 910 illustrated in FIG. 9-A) for detecting the location of the phantom or a module of the phantom and then perform the selective scanning based on the detected location and the location of the first part in the phantom.

In some embodiments, the whole phantom or part of the phantom may be scanned, and the image data received by the performance analyzing module 440 may relate to all the test components included in the phantom. The scanning process may be performed over the whole scan region that the scanner 110 is able to scan or the scan region where the phantom is placed. The determination of the location of the phantom may be made by the user or the performance analyzing module 440 based on one or more positioning parameter obtained by the positioning parameter acquiring sub-module 441 in step 820.

The image data may be generated based on the scan data acquired by a scanner 110. The scan data relating to the first part of the phantom acquired by the scanner 110 may be received by the input/output module 410. The image processing module 430 or the image generating sub-module 443 may generate the image data based on the scan data and then transmit the image data to the performance analyzing module 440.

In some embodiments, the scanner 110 and the performance analyzing module 440 may belong to different systems. For example, the performance analyzing module 440 may belong to a server implemented on a cloud, and the scanner 110 may belong to a local imaging system. The input/output module 410 of the processing engine 140 may receive the scan data collected by the scanner 110, and the image data may be generated by the processing engine 140 based on the scan data. Alternatively, the input/output module 410 of the processing engine 140 may receive the image data generated based on the scan data by the local imaging system.

In 820, the positioning parameter acquiring sub-module 441 may obtain at least one positioning parameter indicative of a positioning manner of the phantom during the scanning. Step 820 may be performed prior to the step 810 in some embodiments.

In some embodiments, the positioning parameter acquiring sub-module 441 may acquire the at least one positioning parameter from a user. The positioning parameter acquiring sub-module may generate a request for the at least one positioning parameter through the terminal 130 to the user. The user may then input the required positioning parameter through the terminal 130.

In some embodiments, the positioning parameter acquiring sub-module 441 may acquire the positioning parameter(s) from a storage device (e.g., the storage 150, the storage 220, or the storage 390). For example, the phantom may be installed on the table 114 through a fixing structure (e.g., the fixing structure 610). The fixing structure may connect to one or more certain structures (e.g., one or more holes or protruding structure) of the table 114. The phantom may have predetermined positioning manner (e.g., the location and the angle relative to the scanner 110) after the installation. The positioning parameter(s) may then be measured once and then save in the storage device for further use or be directly included in the structural information provided with the phantom.

In some embodiments, the positioning parameter acquiring sub-module 441 may obtain one or more positioning parameters during the scanning in real time. For demonstration purposes, an exemplary process for obtaining one or more positioning parameters is described below in connection with FIGS. 9-A to 11-B. This process may be used to obtain one or more positioning parameters relating to a phantom place freely on the table 114 or a phantom installed at a predetermined location of table 114. The obtained positioning parameter(s) may be used for determining the part(s) (e.g., the first part) of the phantom to be scanned, or be used for reducing or eliminating the error occurred during the determination of ROI(s) (e.g., the first ROI).

In some embodiments, the one or more positioning parameters may include one or more reference points of the phantom and/or one or more slopes of the phantom relative to one or more directions.

In 830, the image processing module 430 or image generating sub-module 442 may generate a test image (a first test image) based on the received image data for ROI determination. The first test image may be a volume image or a slice image. The first test image may show a scanned portion (e.g., the first part) of the phantom and one or more first test components included within. The generated first test image may be stored (e.g., in the storage 150, the storage 220, the memory 360, or the storage 390) for further use.

In some embodiments, only one first test component may be shown in the first test image. For example, the first test image may have the center (precisely or approximately) at the central point of the first test component, and a majority of the image region of the first test image may represent the first test component. Alternatively, the first test image may be a cross-sectional image of the phantom with image region representing the first test component.

In some embodiments, a plurality of first test component may be shown in the first test image. The first test image may be a cross-sectional image of the phantom with image regions representing the plurality of first test components.

In some embodiments, due to the positioning manner of the phantom during the scanning, an image generated based on the received image data may be tilted and/or translated. The image processing module 430 or image generating sub-module 442 may generate the first test image further based on the at least one positioning parameter acquired in step 820. Exemplary processes for generating the first test image based on the at least one positioning parameters are discussed below in connection with FIGS. 14-A, 14-B, and 15-A.

In 840, the ROI determining sub-module 443 may determine a first ROI corresponding to the first test component in the first test image generated in step 830 based on the at least one positioning parameter acquired in step 820.

A locating point (the first locating point) corresponding to a point (e.g., a central point) of the first test component may be determined in the first test image based on the at least one positioning parameter for determining the first ROI. The ROI determining sub-module 443 may determine the first ROI based on the first locating point.

In some embodiments, the first locating point may be determined by the image generating sub-module 442 during the generation of the first test image in 830. Alternatively or additionally, the first locating point may be determined by the ROI determining sub-module 443 after the first test image is generated. The first locating point may be determined based on the at least one positioning parameter (e.g., a reference point) and the structural information of the phantom. Exemplary processes are discussed below in connection with FIG. 14-A to 17.

In some embodiments, the first ROI may be determined directly based on the locating point. For example, the first ROI may be determined to have the center (precisely or approximately) at the first locating point. The shape of the first ROI may be determined based on the shape of the first test object (e.g., the ROIs 771 to 766) or be an arbitrary shape (e.g., the ROI 767). The size of the first ROI may also be determined based on the size of the first test object. For example, in a slice image, for the first test object having a circular cross-section with a radius of $r_1$, the first ROI may be determined as a circular region having the center at the first locating point corresponding to the central point of the first test object with a radius equal to a smaller than $r_1$. The radius may be set as a predetermined number (e.g., $r_2$) or a predetermined portion of $r_1$ (e.g., 0.8 $r_1$). The shape and/or size of the first test object may be included in the structural information of the phantom.

In some embodiments, for reducing or eliminating possible errors, the ROI determining sub-module 443 may first determine a first preliminary ROI in the first test image based on the first locating point, and then determine the first ROI within the first preliminary ROI.

In some embodiments, the steps 830 and 840 may be performed based on process 1300 illustrated in FIG. 13.

In 850, the analyzing sub-module 444 may analyze the imaging performance of the imaging system 100 based on the determined first ROI. The analyzing sub-module 444 may analyze one aspect of the imaging performance of the imaging system 100 based on one first ROI when the related first test module includes only one first test component. The analyzing sub-module 444 may analyze one aspect of the imaging performance of the imaging system 100 based on a plurality of first ROIs when the related first test module includes multiple first test components (e.g., a first test module for testing the linearity).

In some embodiments, the first test module may include multiple first test components. Step 840 may be performed for multiple times to determine a plurality first ROIs for analyzing the first aspect of the imaging performance.

In some embodiments, the first part of the phantom may further include a second test module, which may include one or more second test components. The second test module may relate to a second aspect of the imaging performance. The process 800 may further include process 2000 (as illustrated in FIG. 20) for analyzing the first aspect and the second aspect of the imaging performance based on the same image data received by the performance analyzing module 440.

In some embodiments, the phantom may further include a second part that may include a third test module, which may include one or more third test components. The first part and the second part may be physically connected or separated. The third test module may relate to a third aspect of the imaging performance. The image data received by the performance analyzing module may be generated based on a scanning, by the scanner, of both the first part and the second part of the phantom. The process 800 may further include process 2100 (as illustrated in FIG. 21) for analyzing the first aspect and the third aspect of the imaging performance based on the same image data.

It may be noticed that the above description of the process 800 is only for illustration purposes and is not intended to limit the present disclosure. It is understandable that, after learning the major concept and the mechanism of the present disclosure, a person of ordinary skill in the art may alter the process 800 in an uncreative manner. The alteration may include combining and/or splitting certain steps, adding or removing optional steps, changing the performing sequence of the steps, or the like, or a combination thereof. For example, step 820 may be performed before step 810; steps 830 and 840 may be combined into one step. However, the legal protection scope will be defined by the description of claims.

FIG. 9-A is a schematic diagram illustrating an exemplary technique for obtaining one or more positioning parameters according to some embodiments of the present disclosure. A phantom 900 may be fixed or placed on the table 114 during the scanning performed by the scanner 110. The phantom 900 may include one or more positioning modules 920. The gantry 111 of the scanner 920 may be installed with one or more detectors 910 for detecting the one or more positioning modules 920. The one or more detectors may be installed at a location within or prior to the detecting region 113. The scanning may be performed in the direction of the z axis.

The one or more positioning modules 920 may have any proper shapes and/or sizes. A positioning module 920 may be positioned at an appropriate location of the phantom 900. FIG. 9-B is a schematic diagram illustrating exemplary locations of one or more positioning modules of a phantom according to some embodiments of the present disclosure. For example, a positioning module 920 may be positioned at a proper location at the lateral side of the phantom 900, at the top or bottom side (relative to the z axis) of the phantom 900, or inside the phantom 900. The location(s) and the related information (e.g., name, serial number, size, shape) of the positioning module(s) may be included in the structural information of the phantom 900. In some embodiments, the positioning module 920(s) may be positioned on the fixing structure (e.g., the fixing structure 610) used for fixing the phantom 900 on the table 114.

The detector 910 may emit a scanning ray or scan wave for detecting the presence of one or more positioning modules 920, detecting the distance between the detector 910 and one or more positioning modules 920, and/or the direction of one or more positioning modules 920 relative to the detector 910. The scanning ray or scan wave may cover a detecting region 915. The detecting region 915 may be a line, a cone, a plane (e.g., by periodically changing the emitting angle of the scan ray or scan wave), a volume space at least partially covering the scan region, or the like. The scanning ray or scan wave emitted by the detector 910 may be a laser in some embodiments. Alternatively or additionally, the one or more positioning modules 920 may emit a ray or wave to be detected by the detector 910 which may be used for detecting the present or the distance.

One or more positioning parameters may be obtained by the positioning parameter acquiring sub-module 441 according to the information related to the detection by the detector 910. Additionally or alternatively, the part of phantom to be scanned may also be determined using the detector 910. The part to be scanned may refer to the first part of the phantom and/or the second part of the phantom. Exemplary processes are described below in connection with FIGS. 10-A to 11-B.

FIGS. 10-A and 10-B are schematic diagrams illustrating exemplary reference points in the image according to some embodiments of the present disclosure. A phantom 1000 may include one or more sections (e.g., the sections 1001, 1002, and 1003). The phantom 1000 may further include one or more positioning modules for indicating the location of the one or more sections in the phantom and/or in the scan region of the scanner 110.

In the embodiments illustrated in FIG. 10-A, the phantom 100 may include a plurality of positioning modules (e.g., the positioning modules 1011, 1012, 1013). Each positioning module may correspond to a section of the phantom. For example, the positioning module 1011 may correspond to the section 1001, the positioning module 1012 may correspond to the section 1002, and the positioning module 1013 may correspond to the section 1003. The correspondence between the positioning modules and the sections may be included in the structural information of the phantom 1000. In some embodiments, the positioning module (e.g., the positioning module 1012) may represent the start of a section (e.g., the section 1002) and the end of a previous section (e.g., the section 1001).

When a specific aspect of the imaging performance is to be analyzed, the location of the test component (e.g., the first test component) in the phantom may then be decided (e.g., by the performance analyzing module 440) based on the structural information of the phantom 1000. The test component may be, for example, included in the section 1001. According to the structural information of the phantom 1000, the positioning module 1011 may be determined as an indicator of the part to be scanned. The location of positioning module 1011 in the scan region may then be obtained and used (e.g., by the performance analyzing module 440) to determine the start location and/or the end location (e.g., in the form of coordinates, a time point or a time period) of the part to be scanned in the scan region. For example, the start or end location may be determined at the location of the positioning module 1011, or at a location before or after (e.g., in the direction of the z axis) the location of the positioning module 1011 with a predetermined distance. The predetermined distance may be a default value of the imaging system 100, set by a user, included in the structural information of the phantom 1000, or be decided (e.g., by the scanner 110 and/or the performance analyzing module 440) based on the structural information of the phantom 1000, or the like, or a combination thereof.

The position of positioning module 1011 in the scan region may be obtained by using the detector 910 during or prior the scanning. In some embodiments, the detector 910 may scan at least part of the scan region of the scanner 110. For example, the detector 910 may detect the positioning module 1011 and generate a detecting signal. The detecting signal may then be used (e.g., by the scanner 110, the performance analyzing module 440, or a logical circuit integrated to the detector 910) to obtain the distance between the positioning module 1011 and the detector 911, and the direction of the positioning module 1011 relative to the detector 911. The distance and direction of the positioning module 1011 may be used for determining the location (the start location and/or the end location) of the part to be scanned in the scan region (e.g., by the scanner 110 and/or the performance analyzing module 440). Next, the part to be scanned may be moved to the detecting region 113 by the table 114, or the detecting region 113 may be moved to the location of the part to be scanned by the gantry 111 for performing the scanning over the part to be scanned.

In some embodiments, the detector 910 may scan a planar or linear region adjacent to the detecting region 113. The scanner 110 may first move the positioning module 1011 to the detecting region 113 using the table 114 or move the detecting region 113 to the positioning module 1011 using the gantry 111 without performing the scanning. After the detector 910 detects the presence of the positioning module 1011, the scanner 110 may start (autonomously or controlled by the processing engine 140) the scanning immediately or after a predetermined time period. The scanning may be stopped after a predetermined time period or after being performed over a predetermined region (e.g., in the form of a distance in the direction of the z axis).

In some embodiments, a second positioning module (e.g., the positioning module 1012 or 1013) may be used as the indicator of the end location of the part of the phantom to be scanned. The location of the second positioning module in the scan region may be obtained by the detector 910 (e.g., the detector 910 scanning at least part of the scan region of the scanner 110) for determining (e.g., by the scanner 110 and/or the performance analyzing module 440) the end location of the scan region. Alternatively or additionally, the scanner 110 may end or pause (autonomously or controlled by the processing engine 140) the scanning immediately or after a predetermined time period when the detector 910 (e.g., the detector 910 scanning a planar or linear region adjacent to the detecting region 113) detects the presence of the second positioning module.

In the embodiments illustrated in FIG. 10-B, the phantom 100 may include one positioning module (e.g., the positioning module 1060) indicating the location of a plurality of sections in the phantom and/or in the scan region. One or more distances and directions, which may be included in the structural information of the phantom 100, may be used by the positioning parameter acquiring sub-module 441 for determining the location of the part to be scanned in the phantom and/or in the scan region.

For example, when the target test component is in the section 1001, the location of the positioning module 1060 may be determined as the start location of the part to be scanned; when the target test component is in the section 1002, a location before the location of the positioning module 1060 in the direction of the z axis with a distance of $a_1$ may be determined as the start location.

In some embodiments, the end location of the part of the phantom to be scanned may also be determined by the one positioning module. For example, when the part to be scanned is the section 1002, the end location may be determined as a location before the location of the positioning module 1060 in the direction of the z axis with a distance of $a_3$.

In some embodiments, the scanning may be stopped after a predetermined time period or after being performed over a predetermined region (e.g., in the form of a distance in the direction of the z axis). For example, when the part to be scanned is the section 1002, after performing the scanning over a distance of $a_2$, or a time period corresponding to the distance of $a_2$, the scanner 110 may end or pause (autonomously or controlled by the processing engine 140) the scanning.

The related test component may be, for example, included in the section 1002. According to the structural information of the phantom 1000, the positioning module 1011 may be determined as an indicator of the part of the phantom to be scanned. The location of positioning module 1011 in the scan region may then be obtained and used (e.g., by the performance analyzing module 440) to determine the start location (e.g., in the form of coordinates, a time point or a time period) and/or the end location of the part to be scanned in the scan region. For example, the start or end location of the part to be scanned may be determined at the location of the positioning module 1011, or at a location before or after (e.g., in the direction of the z axis) the location of the positioning module 1011 with a predetermined distance. The predetermined distance may be a default value of the imaging system 100, set by a user, included in the structural information of the phantom 1000, or be decided (e.g., by the scanner 110 and/or the performance analyzing module 440) based on the structural information of the phantom 1000, or the like, or a combination thereof.

In some embodiments, additional detector(s) 910 may be installed on the scanner 110 for obtaining additional positioning parameter(s) and/or reducing or eliminating possible errors.

In some embodiments, the techniques described herein in connection with FIGS. 10-A and 10-B may be used for performing selective scans on a plurality of sections of the phantom 1000. The plurality of sections may include continuous or connected sections (e.g., the sections 1001 and 1002) and/or separated sections (e.g., the sections 1001 and 1003).

In some embodiments, the techniques described herein in connection with FIGS. 10-A and 10-B may also be used to determine one or more reference points in the image. For example, after the location of the one or more positioning modules in the scan region of the scanner 110 is obtained by one or more detectors 910, the location of a base point in the scan region may be determined by the positioning parameter acquiring sub-module 441 based on the location of the one or more positioning modules in the scan region and the location of the base point relative to the location of one or more positioning modules in the phantom (included in the structural information of the phantom). According to the correlation between the scan region and the image space of the corresponding image, the positioning parameter acquiring sub-module 441 may obtain the location of a reference point corresponding to the base point in the image. The obtained location of the reference point may be directly put into use or be corrected based on one or more other positioning parameters (e.g., one or more slopes of the phantom in one or more directions relative to the scanner 110).

FIGS. 11-A and 11-B are schematic diagrams illustrating exemplary techniques for determining one or more slopes of the phantom relative to the scanner according to some embodiments of the present disclosure. A phantom (e.g., the phantom 1100 and the phantom 1160) may be positioned tilted (e.g., due to error, and/or misoperation issues) during the scanning.

The one or more slopes of the phantom or the slopes of the axis (e.g., the axis 1101 and the axis 1161) of the phantom may be determined based on one or more positioning modules. The determined one or more slopes may include, for example, a first slope, a second slope, and/or a third slope. Merely for demonstration purposes, in the present disclosure, the first slope, the second slope, and the third slope generally refer to the slopes of the phantom relative to the normal direction of the plane XY, the normal direction of plane XZ, and the normal direction of plane YZ, respectively. However, the first slope, the second slope, and the third slope may be the slopes of the phantom relative to other directions as well.

As shown in FIG. 11-A, the phantom 1100 may include a plurality of positioning modules (e.g., the positioning modules 1101, 1102, and 1103), which may locate in different parts of the phantom. A detector 910 may obtain the distance (e.g., $d_1$, $d_2$ and $d_3$) between each positioning module and the detector 910 and the direction (e.g., in the form of an angle relative to one direction) of each positioning module relative to the detector 910. The positioning parameter acquiring sub-module 441 may obtain the one or more slopes of the phantom in one or more directions based on the obtained distances and directions, and the locations of the plurality of positioning modules in the phantom (included in the structural information of the phantom 1100).

In some embodiments, during or before the scanning, the phantom 1100 may approach the detection region 113 with a predetermined speed in the direction of the z axis. The distances and directions of the plurality of positioning modules at different time points may be obtained for determining the one or more slopes for reducing or eliminating possible errors. Alternatively or additionally, additional detector(s) 910 may reside on the scanner 110 for obtaining additional distances and directions of the plurality of positioning modules in order to reduce or eliminate possible errors.

As shown in FIG. 11-B, the phantom 1160 may include a plurality of positioning modules (e.g., the positioning modules 1161, 1162, and 1163), which may locate in different parts of the phantom. One or more detectors 910 may scan a planar or linear region (e.g., the region 1170) adjacent to or within the detecting region 113. During or before the scanning, the phantom 1160 may approach the detection region 130 with a predetermined speed in the direction of the z axis. When a positioning module reaches the region 1170, the corresponding time point or the corresponding location of the region 1170 in the scan region may be recorded by the scanner 110 or the positioning parameter acquiring sub-module 441. As the phantom 1160 passes through the region 1170, a plurality of time points or locations may be recorded and used for determining a plurality of relative distances (e.g., $\Delta_1$ and $\Delta_2$) between two arbitrary positioning parameters by the scanner 110 or the positioning parameter acquiring sub-module 441. The positioning parameter acquiring sub-module 441 may obtain the one or more slopes of the phantom in one or more directions based on the obtained relative distances and the locations of the plurality of positioning modules in the phantom (included in the structural information of the phantom 1160).

In some embodiments, the plurality of positioning modules as shown in FIGS. 11-A and 11-B may be different parts of the same positioning module. The different parts may be distinguishable for the one or more detectors 910. For example, the different parts may have different materials, shapes, colors, patterns and/or sizes, etc. The locations or orientations of the different parts in the phantom may be included in the structural information of the phantom.

In some embodiments, the positioning modules illustrated in FIGS. 10-A, 10-B, 11-A, and 11-B may be the same type or different types. In some embodiments, the positioning modules illustrated in FIGS. 10-A, 10-B, 11-A, and 11-B may have same, similar or different sizes, shapes, colors, materials, etc.

In some embodiments, a positioning module of the phantom may be used for both the determination of the part to be scanned (and/or the determination of a reference point in the image) and the determination of the one or more slopes.

In some embodiments, optionally, the positioning parameter acquiring sub-module 441 may use the obtained one or more slopes to correct the reference point determined in the process as shown in FIGS. 10-A and 10-B.

It may be noticed that, the descriptions and drawings related to the numbers, sizes, shapes, and/or locations of the positioning parameters, phantoms, and the detectors in FIGS. 9-A to 11-B and the positioning parameter acquiring techniques described above are only for demonstration purposes and are not intended to limit the scope of the protection scope of the present disclosure.

FIG. 12 is a schematic diagram illustrating an exemplary ROI determining sub-module according to some embodiments of the present disclosure. ROI determining sub-module 1200 may be an example of the ROI determining sub-module 443. The ROI determining sub-module 1200 may determine a preliminary ROI in an image (e.g., the first test image) and determine the ROI within the preliminary ROI. ROI determining sub-module 1200 may include a preliminary ROI determining unit 1220 and an ROI determining unit 1230.

The preliminary ROI determining unit 1220 may determine the preliminary ROI based on a locating point. The locating point may correspond to a central point of the target test component (e.g., the first test component). The locating point may be determined by the preliminary ROI determining unit 1220 or by the image generating sub-module 442 during the generating of the corresponding test image.

The ROI determining unit 1230 may determine the ROI within the preliminary ROI. The ROI determining unit 1230 may determine the ROI with centroid based and/or image-segmentation based techniques.

In some embodiments, steps 830 and 840 of the process 800 may be performed based on an exemplary process for generating a test image of a phantom and determining an ROI in the test image illustrated in FIG. 13. FIG. 13 is a flowchart of an exemplary process of determining an ROI in a test image according to some embodiments of the present disclosure. Process 1300 may be repeated for determining multiple ROIs based on the received image data of the phantom. For demonstration purposes, the process 1300 may mainly focus on the generation of the first test image and the determination of the corresponding first ROI(s).

In 1310, the image generating sub-module 442 and/or the image processing module 430 may generate the first test image based on the image data and at least one positioning parameter. The first test image may show the scanned portion (e.g., the first part) of the phantom and the scanned portion(s) of at least one first test components belonging to a first module (single-component or multi-component).

In 1320, the preliminary determining unit 1220 may determine a first preliminary ROI in the first test image generated in 1310. The generated first preliminary ROI may include an image region representing a scanned portion of the first test component. In some embodiments, the first test image may show a plurality of first test components of a first test module, and the preliminary determining unit 1220 may determine a plurality of corresponding first preliminary ROIs.

Steps 1310 and 1320 may be performed similarly or differently for the first test module with one first test component or with multiple first test components. Some preferable embodiments relating to a single-component first test module are discussed in connection with FIGS. 14-A, 14-B, and 16. Some preferable embodiments relating to a multi-component first test module are discussed below in connection with FIGS. 15-A, 15-B, and 17. It may be noticed that these embodiments may be performed on both types of first test modules.

In 1330, the ROI determining unit 1230 may determine the first ROI based on the first preliminary ROI. The determination may be made through centroid based techniques and/or image segmentation based techniques. An exemplary image segmentation based technique is discussed below in connection with FIG. 19-A, and an exemplary centroid based technique is discussed below in connection with FIG. 19-B.

In some embodiments, step 1310 of process 1300 may be performed based on an exemplary process of generating a first test image based on the image data and the at least one positioning parameter illustrated in FIG. 14-A. FIG. 14-A is a flowchart of an exemplary process of generating a first test image based on the image data and the at least one positioning parameter according to some embodiments of the present disclosure. Process 1400 may be preferably adopted when the first testing module consists only one first testing component. Alternatively or additionally, the process 1400 may also be adopted in the occasion that the first testing module includes multiple first testing components and one first test image is generated for each first test component.

One or more steps of the process 1400 may be carried out by the image processing module 430 and/or the image generating sub-module 442. For purposes of illustration only, the process 1400 is described in connection with Process I illustrated in FIG. 16, which is a schematic diagram illustrating an exemplary process for generating a first test image based on the image data and the at least one positioning parameter according to some embodiments of the present disclosure.

In 1410, the image processing module 430 and/or the image generating sub-module 442 may be configured to generate a first preliminary test image based on a first reference point (e.g., the point 1631) and the image data received by the performance analyzing module 440. The first image data may relate to a scanning of the first part of a phantom (e.g., the phantom 1600 illustrated in FIG. 16) performed by the scanner 110. The first part of the phantom may include a first test component (e.g., the test component 1601).

The first preliminary test image (e.g., the image 1610) described in process 1400 may be a slice image or a volume image of the scanned part of the phantom. The first preliminary test image may include an image region (e.g., the image region 1602) representing the first test component.

The first reference point may correspond to a base point (e.g., the point 1630) in the phantom. The base point may be a central point of the first part of the phantom. The first reference point may be determined according to the disclosure herein in connection with FIGS. 10-A to 11-B. It may be noticed that, due to error, imprecision, and/or misoperation issues, the determined first reference point may not accurately represent the base point in the image data. For example, the determined first reference point may be one or more pixels away from the pixel representing the base point.

The first preliminary test image may be constructed having the center (precisely or approximately) at the first reference point. For example, the reconstruction center of the first preliminary test image may be set as the first reference point by the image generating sub-module 442. As the phantom may not be positioned precisely during the scanning, the generated first preliminary test image may be tilted or distorted due to the positioning manner of the phantom. Consequently, the image region representing the first test image may also be tilted or distorted as shown in the image 1610.

In 1420, the image processing module 430 and/or the image generating sub-module 442 may be configured to process the first preliminary test image based on the first slope and generate a processed image (e.g., the image 1611). The processed image may be a better cross-sectional view of the phantom compared to the first preliminary test image.

The processed image may have the center at (precisely of approximately) the first reference point, and the tilt or the distortion occurred in the first preliminary test image may be corrected or adjusted in the processed image. Accordingly, the tilt or distortion of the image region (e.g., image region 1622) representing the first test component may also be corrected.

The first slope may be determined according to the disclosure herein in connection with FIGS. 11-A to 11-B.

In some embodiments, the processing of the first preliminary test image may include rotating the first preliminary image. Alternatively or additionally, the processing of the first preliminary test image may include modifying the image data based on the first slope and reconstructing an image (e.g., the processed image) based on the modified image data. The image may be reconstructed with the first reference point set as the reconstruction center.

In 1430, the image generating sub-module 442 may be configured to determine a first locating point (e.g., the point 1640) based on the first reference point, the first slope, and the structural information of the phantom. In some embodiments, step 1430 may be performed before step 1420 or 1410. The first locating point may relate to a target point (e.g., the point 1610) of the first test component. The target point may be the central point of the first test component. It may be noticed that the determined first locating point may not accurately represent the target point in the image data. For example, the determined first reference point may be one or more pixels away from the pixel represent the base point. Errors related to the determined locating points (e.g., the first locating points) are discussed below in connection with FIGS. 18-A to 18-C.

The structural information may include parameters indicating the location of the target point corresponding to the first test component in the phantom. For example, the structural information may include parameters representing the direction and the distance of the target point relative to the base point in the phantom.

In some embodiments, the central point of the first test component may locate right in the x direction of the central point (base point) of the phantom (which may be included in the structural information of the phantom). The first reference point may relate to the central point of the phantom, and the first locating point may be set as relating to the central point of the first test component. For demonstration purposes, the coordinates of the first locating point ($x_{FL}$, $y_{FL}$) in the image data may be obtained by Equations 1 and 2, which may be expressed as:

$$x_{FL}=(x_{FR}-D_x*\sin(\text{Tilt}_{xy})) \quad (1),$$

$$y_{FL}=(y_{FR}+D_x*\cos(\text{Tilt}_{xy})) \quad (2),$$

where $x_{FR}$ and $y_{FR}$ refer to the coordinates of the first reference point in the image, $D_x$ refers to the distance from the central point of the phantom to the central point of the first test component, and $\text{Tilt}_{xy}$ refers to the first slope. $x_{FR}$, $y_{FR}$, and $\text{Tilt}_{xy}$ may be obtained as positioning parameters as described in FIGS. 11-A and 11-B. $D_x$ may be included in the structural information of the phantom.

In some embodiments, the image generating sub-module 442 may generate the first test image based on the first locating point in the next step. Alternatively, the image generating sub-module 442 may transmit the data related to the first locating point to the image processing module 430, which may generate the first test image based on the received data in the next step.

In 1440, the image processing module 430 and/or the image generating sub-module 442 may be configured to generate the first test image based on the first locating point. The first test image may be constructed having the center (precisely or approximately) at the first locating point. For example, the reconstruction center of the first test image may be set as the first locating point by the image generating sub-module 442. In some embodiments, the first test image may include an enlarged view (e.g., the image region 1623) of the corresponding first test component.

In some embodiments, the generating of the first test image may include performing scaling and translating on the first preliminary image. Alternatively or additionally, the generating of the first test image may include reconstructing an image (e.g., the first test image) based on the first locating point, the image data, and any other related coefficients (e.g., coefficients deciding the scaling, the scope, the image quality, etc., of the first test image). The image may be reconstructed with the first locating point set as the reconstruction center.

In some embodiments, step 1440 may be omitted, and the first preliminary test image may be designated as the first test image. The first locating point determined in step 1430 may be used to determine the first preliminary ROI in step 1320. Alternatively, the determination of the first locating point may be omitted.

In some embodiments, step 1310 of process 1300 may be performed based on an exemplary process of generating a first test image based on the image data and the at least one positioning parameter illustrated in FIG. 14-B. FIG. 14-B is a flowchart of an exemplary process of generating a first test image based on the image data and the at least one positioning parameter according to some embodiments of the present disclosure. Process 1450 may be preferably adopted when the first testing module consists only one first testing component. Alternatively or additionally, the process 1450 may also be adopted in the occasion that the first testing module includes multiple first testing components and one first test image is generated for each first test component.

One or more steps of the process 1450 may be carried out by the image processing module 430 and/or the image generating sub-module 442. For purposes of illustration only, the process 1450 is described in connection with Process II illustrated in FIG. 16.

In 1460, the image generating sub-module 442 may be configured to determine a first locating point (e.g., the point 1640) in the image data received by the performance analyzing module 440 based on a first reference point, the first slope, and the structural information of the phantom.

The image data may relate to a scanning of the first part of a phantom (e.g., the phantom 1600 illustrated in FIG. 16) performed by the scanner 110. The first part of the phantom may include a first test component (e.g., the test component 1601).

The first reference point may correspond to a base point (e.g., the point 1630) in the phantom. The base point may be a central point of the phantom. The first slope may relate to the slope of the phantom relative to the normal direction of the plane XY. The first reference point and the first slope may be determined according to the disclosure herein in connection with FIGS. 10-A to 11-B. It may be noticed that, due to error, imprecision, and/or misoperation issues, the determined first reference point may not accurately represent the base point in the image data. For example, the determined first reference point may be one or more pixels away from the pixel representing the base point.

The first locating point may relate to a target point (e.g., the point 1610) of the first test component (e.g., the test component 1401). The target point may be the central point of the first test component. It may be noticed that the determined first locating point may not accurately represent the target point in the image data. Errors related to the determined locating points (e.g., the first locating points) are discussed below in connection with FIGS. 18-A to 18-C.

In some embodiments, the image generating sub-module 442 may generate the first test image based on the first locating point in the next step. Alternatively, the image generating sub-module 442 may transmit the data related to the first locating point to the image processing module 430, which may generate the first test image based on the received data in the next step.

The process described by step 1460 is similar to the one described in step 1430 (as illustrated in FIG. 14-A). For more detailed information about step 1460, the description of step 1430 may be referenced.

In 1470, the image processing module 430 and/or the image generating sub-module 442 may be configured to generate a first preliminary test image based on the first locating point and the image data.

The first preliminary test image (e.g., the image 1616) described in the process 1450 may be a slice image or a volume image emphasizing the first test component included in the scanned part of the phantom. The first preliminary test image may be constructed having the center (precisely or approximately) at the first locating point. For example, the reconstruction center of the first preliminary test image may be set as the first locating point by the image generating sub-module 442. In some embodiments, the first preliminary test image may include an enlarged view (e.g., the image region 1614) of the first test component. As the phantom may not be positioned precisely during the scanning, the generated first preliminary test image may be tilted or distorted due to the positioning manner of the phantom. Consequently, the image region representing the first test image may also be tilted or distorted as shown in image 1616.

In 1480, the image processing module 430 and/or the image generating sub-module 442 may be configured to process the first preliminary test image based on the first slope and generate the first test image (e.g., the image 1650). The generated first test image may have the center at (precisely of approximately) the first locating point, and the tilt or the distortion occurred in the first preliminary test image may be corrected or adjusted in the first test image. Accordingly, the tilt or distortion of the image region (e.g., the image region 1623) representing the first test component may also be corrected.

In some embodiments, the processing of the first preliminary test image may include rotating the first preliminary image based on the first slope. Alternatively or additionally, the processing of the first preliminary test image may include modifying the image data based on the first slope and reconstructing an image (e.g., the first test image) based on the modified image data.

In some embodiments, during the process 1450, a cross-sectional image of the phantom may be generated based on the first reference point, the first slop, and the received image data. For example, the first reference point may be set as the reconstruction center of the cross-sectional image. The cross-sectional image may be similar to the image 1610 or the image 1611. The cross-sectional image may be used for preview or overview. The process for generating the cross-sectional image may be similar to the process for generating the image 1610 or the image 1611.

Referring back to FIG. 13, after obtaining the first test image and the first locating point in 1310 according to the process 1400 or 1450, the preliminary ROI determining unit 1220, in 1320, may be configured to determine the first preliminary ROI in the first test image based on the first locating point.

In some embodiments, the first preliminary ROI may have a center (precisely or approximately) at the first locating point and may have predetermined shape (e.g., circle, square) and/or size for covering at least a major part (e.g., more than 80%) of the image region representing the corresponding first test component. Merely by way of example, the first preliminary ROI may be configured as a square having the center at the first locating point with a side length about 150 to 300% of the side length or radius of the corresponding first test component.

In some embodiments, step 1310 of the process 1300 may be performed based on an exemplary process of generating a first test image based on the image data and at least one positioning parameter illustrated in FIG. 15-A.

FIG. 15-A is a flowchart of an exemplary process of generating a first test image based on the image data and at least one positioning parameter according to some embodiments of the present disclosure. Process 1500 may be preferably adopted when the first testing module consists a plurality of first test components. Alternatively or additionally, the process 1500 may also be adopted in the occasion that the first testing module includes multiple first testing components and one first test image is generated for each first test component.

One or more steps of the process 1500 may be performed by the image processing module 430 and/or the image generating sub-module 442. For purposes of illustration only, the process 1500 is described in connection with FIG. 17, which is a schematic diagram illustrating an exemplary process for generating a first test image based on the image data and the at least one positioning parameter according to some embodiments of the present disclosure.

In 1510, the image processing module 430 and/or the image generating sub-module 442 may be configured to generate a first preliminary test image based on a first reference point (e.g., the point 1741) and the image data received by the performance analyzing module 440. The image data may relate to a scanning of the first part of a phantom (e.g., the phantom 1700 illustrated in FIG. 17) performed by the scanner 110. The first part of the phantom may contain a first test module including a plurality of first test components (e.g., the test components 1720 to 1723).

The first preliminary test image (e.g., the image 1760) described in the process 1500 may be a slice image or a volume image of the scanned part of the phantom. The first preliminary test image may include a plurality of image regions (e.g., the image regions 1730 to 1734) representing the plurality of first test components.

The first reference point may correspond to a base point (e.g., the point 1740) in the phantom. The base point may be a central point of the phantom. The first reference point may be determined according to the disclosure herein in connection with FIGS. 10-A to 11-B. It may be noticed that, due to error, imprecision, and/or misoperation issues, the determined first reference point may not accurately represent the base point in the image data. For example, the determined first reference point may be one or more pixels away from the pixel represent the base point.

The first preliminary test image may be constructed having the center (precisely or approximately) at the first reference point. For example, the reconstruction center of the first preliminary test image may be set as the first reference point by the image generating sub-module 442. As the phantom may not be positioned precisely during the scanning, the generated first preliminary test image may be tilted or distorted due to the positioning manner of the phantom. Consequently, the image region representing the first test image may also be tilted or distorted as shown in the image 1760.

In 1520, the image processing module 430 and/or the image generating sub-module 442 may be configured to process the first preliminary test image based on the first slope and generate the first test image (e.g., the image 1770). The generated first test image may be a better cross-sectional view of the phantom compared to the first preliminary test image. The first test image may have the center at (precisely or approximately) the first reference point, and the tilt or the distortion occurred in the first preliminary test image may be corrected or adjusted in the first test image. Accordingly, the tilt or distortion of the image regions (e.g., the image regions 1740 to 1743) representing the plurality of first test components may also be corrected.

The first slope may be determined according to the disclosure herein in connection with FIGS. 11-A to 11-B.

In some embodiments, the processing of the first preliminary test image may include rotating the first preliminary image. Alternatively or additionally, the processing of the first preliminary test image may include modifying the image data based on the first slope and reconstructing an image (e.g., the processed image) based on the modified image data. The image may be reconstructed with the first reference point set as the reconstruction center.

Referring back to FIG. 13, after obtaining the first test image, the preliminary ROI determining unit 1220, in 1320, may determine the first preliminary ROI in the first test image. In some embodiments, step 1320 of the process 1300 may be performed based on an exemplary process of exemplary process of determining a first preliminary ROI in the first test image illustrated in FIG. 15-B. FIG. 15-B is a flowchart of an exemplary process of generating a first preliminary ROI in the first test image according to some embodiments of the present disclosure. Process 1550 may be performed after the process 1500. One or more steps of the process 1550 may be performed by the preliminary ROI determining unit 1220.

In 1550, the preliminary ROI determining unit 1220 may be configured to determine a first locating point based on the first reference point adopted in process 1500 (e.g., the point 1741), the first slope, and the structural information of the phantom.

The first locating point may relate to a target point (e.g., the point 1762) of one of the plurality of first test components (e.g., the test component 1722). The target point may be the central point of the first test component. It may be noticed that the determined first locating point may not accurately represent the target point in the image data. Errors related to the determined locating points (e.g., the first locating points) are discussed below in connection with FIGS. 18-A to 18-C.

Step 1550 is similar to step 1430 (as illustrated in FIG. 14-A), the description of which can be elsewhere in this disclosure.

In 1560, the preliminary ROI determining unit 1220 may be configured to determine the first preliminary ROI in the first test image based on the first locating point. In some embodiments, the first preliminary ROI may have a center (precisely or approximately) at the determined first locating point and may have predetermined shape (e.g., circle, squire) and or size for covering at least a major part (e.g., more than 80%) of the image region representing the corresponding first test component.

In some embodiments, the process 1550 may be repeated for multiple times for obtaining a plurality of first preliminary ROIs corresponding to the plurality of first test components in the first test image. A first ROI may be determined for each first preliminary ROI for determining one aspect of the imaging performance of the imaging system 100

FIGS. 18-A, 18-B, and 18-C are schematic diagrams illustrating exemplary errors relating to the determined locating points (e.g., the first locating points). Image 1800, 1801, and 1802 may each be a part of a test image (e.g., a first test image) showing a test component (e.g., a first test component). The determined locating points 1820, 1821, 1822, and 1823 may correspond to the central point of the corresponding test component.

In the cases as illustrated in FIG. 18-A, the determined locating point (e.g., the point 1820) in the image may be at (precisely or approximately) the center of the image region (e.g., the image region 1810) representing the test component.

In other cases, however, due to error, imprecision and/or misoperation issues, the determined locating point in the image may deviate from the actual location. For example, in some cases illustrated in FIG. 18-B, the deviated locating point (e.g., the point 1821) may still locate within the image region (e.g., the image region 1811) representing the corresponding test component. As another example, in some extreme cases illustrated in FIG. 18-C, the deviated locating point (e.g., the point 1822) may locate outside the image region (e.g., the image region 1812) representing the corresponding test component.

The error, imprecision and/or misoperation issues may relate to, for example, the manufacturing of the phantom, the measuring of the related parameters, the installing of the phantom, the registering of the structural information, the inputting of structural information into the processing engine 140, the obtaining of positioning parameters, the determining of the related reference point, or the like, or a combination thereof.

In the cases illustrated in FIG. 18-A, or when the deviated locating point still locates very close to the actual location, the ROI determining sub-module 443 may determine an ROI based on the locating point without determining any preliminary ROI. In some embodiments, the first ROI may be determined to have a center (precisely or approximately) at the first locating point and may have a predetermined shape (e.g., circles, squares) and/or size within the image region representing the corresponding first test component. The determined ROI and the corresponding image region may have similar or different shapes. The determined ROI may have the same size, or a smaller size (e.g., 50% to 90%) compare to the corresponding image region.

In the cases illustrated in FIGS. 18-B and 18-C, the ROI determining sub-module 443 may first determine a preliminary ROI based on the deviated locating point and determine the ROI within the preliminary ROI.

FIGS. 19-A and 19-B are schematic diagrams illustrating exemplary ROIs according to some embodiments of the present disclosure. For demonstration purposes, the ROI determining techniques may be described based on the cases illustrated in FIG. 18-B. However, the ROI determining techniques illustrated in FIGS. 19-A and 19-B may also be applied in the extreme cases illustrated in FIG. 18-C and the the cases illustrated in FIG. 18-A (e.g., in a batch processing or for precaution purposes). The ROI determining process may be performed by the ROI determining unit 1230.

Image 1901 may be a part of a test image (e.g., a first test image) showing a test component (e.g., a first test component). A first locating point 1921, which may be deviated from the actual location, may be determined in the test image. A preliminary ROI 1923 may be determined based on the deviated first locating point 1921. The preliminary ROI 1931 may include the image region (image region 1911) representing the corresponding test component. The deviated first locating point 1921, and the preliminary ROI 1911 may be determined according to process 1300, 1400, 1450 and/or 1550.

As illustrated in FIG. 19-A, within the preliminary ROI 1931, the ROI determining unit 1230 may determine the ROI 1923 based on the image segmentation technique. The image segmentation technique may be based on clustering, compression, histogram, edge detection, dual clustering, region growing, partial differential equation, graph partitioning, watershed transformation, neural network, or the like, or a combination thereof.

In an exemplary segmentation method, the ROI determining unit 1230 may determine the edge of the image region 1911 within the preliminary ROI 1931. The ROI determining unit 1230 may also designate the image region within the determined edge of the image region 1911 as the determined ROI 1923.

Another technique for determining the ROI is illustrated in FIG. 19-B. Within the preliminary ROI 1931, the ROI determining unit 1230 may determine the centroid (e.g., in the form of coordinates, a pixel, a voxel) of the image region covered by the preliminary ROI 1931. In some embodiments, the centroid may be determined through image moment-based techniques.

The determined centroid (e.g., the point 192) may be at (precisely or approximately) or more adjacent to the center of the image region 1911. The ROI determining unit 1230 may determine an ROI (e.g., the ROI 1930) based on the centroid. The determined ROI may partially or fully cover the image region 1911. In some embodiments, the determined ROI may have a center (precisely or approximately) at the centroid; the shape of the ROI may be determined based on the shape of the corresponding test object or be an arbitrary shape; the size of the first ROI may be determined based on the size of the corresponding test object. The shape and/or size of the corresponding test component may be included in the structural information of the phantom.

In some embodiments, a new image may be generated by the image processing module 430, the image generating sub-module 442, or the ROI determining unit 1230 based on the determined centroid and the image data received by the performance analyzing module 440. The new image may have the center at (precisely or approximately) the determined centroid with a predetermined shape and/or size. The new image may be used for preview, overview, or the determination of the first ROI.

In some embodiments, the first part of the phantom may further include a second test module including one or more second test components. The second test module may relate to a second aspect of the imaging performance. Process 800 illustrated in FIG. 8 may further include an exemplary process (process 2000) of determining a second ROI (corresponding to a second test component) based on the received image data illustrated in FIG. 20 for determining the imaging performance of the imaging system 100 further based on the second ROI. One or more steps of the process 2000 may be carried out by one or more sub-modules of the performance analyzing module 440.

In 2010, the ROI determining sub-module 443 may obtain a second test image. The second test image may be a volume image or a slice image. The second test image may show a scanned portion (e.g., the first part) of the phantom and one or more second test components included within.

In some embodiments, the second test image may be generated by the image processing module 430 and/or image generating sub-module 442 based on the image data received in 810. The process for generating the second test image is similar to the process for generating the first test image (e.g., the process 1400 illustrated in FIG. 14-A, the process 1450 illustrated in FIG. 14-B, and the process 1500 illustrated in FIG. 15-A), which is described elsewhere in this disclosure.

In some embodiments, the first test image showing the cross-sectional view of the phantom may be directly designated or used as the second test image. The ROI determining sub-module 443 may obtain the stored first test image via the input/output module 410 (e.g., from the storage 150, the storage 220, the memory 360, or the storage 390).

In 2020, the ROI determining sub-module 443 may determine a second ROI corresponding to the second test component in the second test image obtained in step 2010 based on the at least one positioning parameter acquired in step 820. The process for determining the second ROI is similar to the process for determining the first ROI (e.g., the process 1300 illustrated in FIG. 13), which is described elsewhere in this disclosure.

In 2030, the analyzing sub-module 444 may analyze the imaging performance of the imaging system 100 based on the determined first ROI and the second ROI.

In some embodiments, the first ROI and the second ROI may be used for determining different aspects (e.g., the first aspect and the second aspect) of the imaging performance of the imaging system 100.

In some embodiments, the second test module may relate to both the first and the second aspect of the imaging performance of the imaging system 110. The first ROI and the second ROI may be used for determining the same aspect (the first aspect) of the image performance of the phantom. The second ROI may be optionally used for determining the second aspect of the imaging performance of the imaging system 100.

In some embodiments, the phantom may further include a second part which may include a third test module including one or more third test components. The first part and the second part may be connected or separated. The third test module may relate to a third aspect of the imaging performance. The image data received by the performance analyzing module may be generated based on a scanning, by the scanner, of both the first part and the second part of the phantom. Process 800 illustrated in FIG. 8 may further include an exemplary process (process 2100) of determining a third ROI (corresponding to a third test component) based on the received image data as illustrated in FIG. 21 for determining the imaging performance of the imaging system 100 further based on the third ROI. One or more steps of process 2100 may be carried out by one or more sub-modules of the performance analyzing module 440.

In 2110, the image processing module 430 and/or image generating sub-module 442 may generate a third test image based on the received image data and the at least one positioning parameter. The third test image may be a volume image or a slice image. The third test image may show a scanned portion (e.g., the second part) of the phantom and one or more third test components included within.

In some embodiments, the third test image may be generated based on a second reference point, the image data, and the first slope. The second reference point may correspond to a base point (e.g., a central point) of the second part of the phantom. The process for generating the third test image is similar to the process for determining the first ROI (e.g., the process 1400 illustrated in FIG. 14-A, the process 1450 illustrated in FIG. 14-B, and the process 1500 illustrated in FIG. 15), which is described elsewhere in this disclosure.

The second reference point may be directly obtained according to the technique described in connection with FIGS. 10-A to 11-B. Alternatively, the second reference point may be obtained based on the first reference point, the structural information of the phantom, the second slope and the third slope of the phantom (which may be obtained in step 820).

In some embodiments, the base points corresponding to the first reference point and the second reference point may be the central points of the phantom. For demonstration purposes, the coordinates of the second reference point ($x_{SR}$, $y_{SR}$) in the image data may be obtained by Equations 3 and 4, which may be expressed as:

$$x_{SR}=(x_{FR}+L*\tan(\text{Tilt}_{xz})) \quad (3),$$

$$y_{SR}=(y_{FR}+L*\tan(\text{Tilt}_{yz})) \quad (4),$$

where $x_{FR}$ and $y_{FR}$ refer to the coordinate of the first reference point in the image, $L_z$ refers to the distance between the base points corresponding to the first reference point and the second reference point, $\text{Tilt}_{xz}$ refers to the second slope, and $\text{Tilt}_{yz}$ refers to the third slope. $x_{FR}$, $y_{FR}$, $\text{Tilt}_{xz}$, and $\text{Tilt}_{yz}$ may be obtained as positioning parameters as described elsewhere in this disclosure (e.g., the description herein in connection with FIGS. 11-A and 11-B).

In some embodiments, the third test module and the first test module may be different test modules. $L_z$ may be included in the structural information of the phantom.

In some embodiments, the third test module and the first test module may refer to the same test module (or different scanned portions of the same test module). The second part and the first part of the phantom may refer to different parts of the same section of the phantom. $L_z$ may be a scanning parameter (e.g., the slice thickness) determined by a user, the scanner 110, and/or the performance analyzing module 440.

In 2120, the ROI determining sub-module 443 may determine a third ROI corresponding to the third test component in the third test image obtained in step 2110 based on at least one positioning parameter (e.g., the one acquired in step 820). The process for determining the third ROI is similar to the process for determining the first ROI. The related description of determining the first ROI may be referenced in this step.

In 2130, the analyzing sub-module 444 may analyze the imaging performance of the imaging system 100 based on the determined first ROI and the third ROI.

In some embodiments, the third test module and the first test module may refer to different test modules. The second part and the first part of the phantom may relate to different sections (e.g., the sections 531 to 533, 541 to 543) of the phantom. The first ROI and the third ROI may be used for determining different aspects of the imaging performance of the imaging system 100.

In some embodiments, the third test module and the first test module may refer to the same test module (or different scanned portions of the same test module). The second part and the first part of the phantom may refer to different parts of the same section of the phantom. For example, referring to FIG. 7-B, the first part may be the part of phantom between cross-sections 751 and 753, and the second part may be the part of phantom between cross-sections 753 and 754. The first ROI and the third ROI may be used for determining the same aspect of the image performance of the imaging performance of the imaging system 100.

FIGS. 22, 23, and 24 illustrate images generated according to an embodiment of the present disclosure. Image 2200 is generated base on a scanning of a phantom performed by a CT scanner. The image 2200 shows a cross-section of a first section of the phantom, which includes a plurality of test modules for analyzing different aspects of the imaging performance of the CT scanner. Image 2200 may correspond to image 1611 or image 1770 given the test module (single-component or multi-component) used.

Image 2300 is generated based on image 2200. Image 2300 shows a test component (or a single-component test module) used for analyzing the MTF property of the CT scanner. Image 2300 may correspond to image 1650.

Image 2400 and image 2200 are generated base on the same scanning. Image 2200 shows a cross-section of a second section of the phantom, which is mostly occupied by a test component (or a single-component test module). The reference point (the second reference point) for generating the image 2400 is determined based on the reference point (the first reference point) for generating the image 2200.

It should be noted that the present disclosure may be implemented in software or a combination of software and hardware; for example, it may be implemented by a dedicated integrated circuit (ASIC), a general-purpose computer, or any other similar hardware device. In an embodiment, the software program of the present disclosure may be executed by a processor so as to implement the above steps or functions. Likewise, the software program of the present disclosure (including relevant data structure) may be stored in a computer-readable recording medium, for example, a RAM, a magnetic or optical driver, or a floppy disk, and similar devices. Besides, some steps of functions of the present disclosure may be implemented by hardware, for example, a circuit cooperating with the processor to execute various functions or steps.

In addition, part of the present disclosure may be applied as a computer program product, e.g., a computer program instruction, which, when being executed by a computer, may invoke or provide a method and/or technical solution according to the present application through the step of the computer. The program instruction that invokes a method of the present application may be stored in a fixed or mobile recording medium, and/or transmitted through broadcast and/or a data flow in other signal carrier medium, and/or stored in a work memory running according to the program instruction in a computer device. Here, an embodiment according to the present application includes an apparatus that includes a memory for storing computer program instructions and a processor for executing program instructions, wherein when being executed by the processor, the computer program instruction triggers the apparatus to carry out the methods and/or technical solutions according to various embodiments of the present application.

To those skilled in the art, it is apparent that the present disclosure is not limited to the details of the above exemplary embodiments, and the present disclosure may be implemented in other forms without departing from the spirit or basic features of the present disclosure. Thus, in any way, the embodiments should be regarded as exemplary, not limitation; the scope of the present disclosure is limited by the appended claims, instead of the above depiction. Thus, all variations intended to fall within the meaning and scope of equivalent elements of the claims should be covered by the present disclosure. No reference signs in the claims should be regarded as limiting the involved claims. Besides, it is apparent that the term "comprise/comprising/include/including" does not exclude other units or steps, and singularity does not exclude a plurality. A plurality of units or means stated in the apparatus claims may also be implemented by a single unit or means through software or hardware. Terms such as the first and the second are used to indicate names but do not indicate any particular sequence.

What is claimed is:

1. A method for determining a region of interest (ROI) for analyzing performance of an imaging device, the imaging device including a scanner, the method being implemented on at least one device each of which has at least one processor and a storage, the method comprising:
receiving, by the at least one processor, image data related to a scanning, by the scanner, of a first part of a phantom, the first part of the phantom including at least part of a first test component, and the first test component being used for analyzing imaging performance of the imaging system;
obtaining, by the at least one processor, at least one positioning parameter indicative of a positioning manner of the phantom during the scanning;
generating, by the at least one processor, a first test image based on the received image data; and
determining, by the at least one processor, a first ROI relating to the first test component in the first test image based on the at least one positioning parameter.

2. The method of claim 1, wherein the phantom further includes one or more positioning components, the method further comprising:
determining, based on the one or more positioning components, at least one of the first part of the phantom, or the at least one positioning parameter.

3. The method of claim 1, determining the first ROI based on the image data and the at least one positioning parameter comprising:
generating the first test image based on the image data and the at least one positioning parameter, the first test image showing a scanned portion of a first test device of the phantom, the first test device including the first test component;
determining a first preliminary ROI in the first test image, the first preliminary ROI including an image region representing a scanned portion of the first test component; and
determining the first ROI based on the first preliminary ROI.

4. The method of claim 3, determining the first ROI based on the first preliminary ROI comprising:
determining a centroid of the first preliminary ROI; and
determining the first ROI based on the centroid.

5. The method of claim 3, wherein:
the at least one positioning parameter includes a first reference point corresponding to a first point within the first part of the phantom and a first slope of the phantom relative to a first direction;
a cross-section of the phantom at which the first point locates cuts through the first test component;
the first test device includes a plurality of first test components; and the method further includes:
  generating a first cross-sectional image of the phantom based on the first reference point, the first slope, and the image data, wherein
    the first reference point is set as a reconstruction center of the first cross-sectional image, and
    the first cross-sectional image is designated as the first test image;
  determining, for each of the first test components, a second locating point within the first test image based on the first reference point, the first slope, and structural information of the phantom indicating the location of the each of the first test components in the phantom;
  generating, for the each of the first test components, a first preliminary ROI based on the corresponding second locating point;
  obtaining, for the each of the first test components, a first ROI based on the first preliminary ROI; and
  analyzing performance of the imaging device based on the obtained first ROIs for the plurality of the first test components.

6. The method of claim 3, determining the first preliminary ROI in the first test image including:
  determining a first locating point based on the at least one positioning parameter and structural information of the phantom indicating the location of the first test component in the phantom; and
  determining the first preliminary ROI based on the first locating point.

7. The method of claim 3, generating the first test image based on the image data and the at least one positioning parameter comprising:
  determining a first locating point based on the at least one positioning parameter and structural information of the phantom indicating the location of the first test component in the phantom; and
  generating the first test image based on the first locating point, wherein the first locating point is set as a reconstruction center of the first test image.

8. The method of claim 1, wherein the scanned first part of the phantom further includes at least part of a second test component, the method further comprising:
  obtaining a second test image showing a scanned portion of a second test device, the second test device including the second test component;
  determining a second ROI relating to the second test component in the second image based on the at least one positioning parameter; and
  analyzing performance of the imaging device based on the first ROI and the second ROI.

9. The method of claim 1, wherein the phantom further includes a second part that includes a third test component, the received image data relates to the scanning of both the first part and the second part of the phantom, the method further comprising:
  generating, by the at least one processor, a third test image based on the received image data and the at least one positioning parameter;
  determining, by the at least one processor, a third ROI relating to the third test component in the third test image based on the at least one positioning parameter; and
  analyzing, by the at least one processor, performance of the imaging device based on the first ROI and the third ROI.

10. The method of claim 9, wherein:
  the at least one positioning parameter includes a first reference point corresponding to a first point within the first part of the phantom, a first slope of the phantom relative to a first direction, a second slope of the phantom relative to a second direction, and a third slope of the phantom relative to a third direction; and
  the determining the third ROI based on the at least one positioning parameter includes:
    determining a second reference point corresponding to a point within the second part of the phantom based on the first reference point, the second slope, the third slope, and structural information of the phantom indicating the location of the second point relative to the first point; and
    generating the third test image based on the second reference point and the first slope, wherein the cross-section of the phantom at which the second point locates cuts through the third test component.

11. A system for determining an ROI for analyzing performance of an imaging device, the system comprising:
  at least one storage device storing instructions; and
  at least one processor being in communication with the at least one storage device, wherein, when executing the instructions, the at least one processor is configured to cause the system to:
    receive image data related to a scanning, by a scanner of the imaging device, of a first part of a phantom, the first part of the phantom including at least part of a first test component, and the first test component being used for analyzing imaging performance of the imaging system;
    obtain at least one positioning parameter indicative of a positioning manner of the phantom during the scanning;
    generate a first test image based on the received image data; and
    determine a first ROI relating to the first test component in the first test image based on the at least one positioning parameter.

12. The system of claim 11, wherein:
  the phantom further includes one or more positioning components;
  the system further includes one or more detectors being configured to detect the one or more positioning components; and
  the at least one processor is further configured to cause the system to determining, based on the one or more positioning components, at least one of the first part of the phantom, or the at least one positioning parameter.

13. The system of claim 11, to determine the first ROI based on the image data and the at least one positioning parameter, the at least one processor is configured to cause the system to:
  generate the first test image based on the image data and the at least one positioning parameter, the first test image showing a scanned portion of a first test device of the phantom, the first test device including the first test component;
  determine a first preliminary ROI in the first test image, the first preliminary ROI including an image region representing a scanned portion of the first test component; and
  determine the first ROI based on the first preliminary ROI.

14. The system of claim 13, to determine the first preliminary ROI in the first test image, the at least one processor is further configured to cause the system to:

determine a first locating point based on the at least one positioning parameter and structural information of the phantom indicating the location of the first test component in the phantom; and determine the first preliminary ROI based on the first locating point.

15. The system of claim 11, wherein:

the at least one positioning parameter includes a first reference point corresponding to a first point within the first part of the phantom and a first slope of the phantom relative to a first direction;

a cross-section of the phantom at which the first point locates cuts through the first test component;

the first test device includes a plurality of first test components; and the at least one processor is further configured to cause the system to:

generate a first cross-sectional image of the phantom based on the first reference point, the first slope, and the image data, wherein the first reference point is set as a reconstruction center of the first cross-sectional image, and the first cross-sectional image is designated as the first test image;

determine, for each of the first test components, a second locating point within the first test image based on the first reference point, the first slope, and structural information of the phantom indicating the location of the each of the first test components in the phantom;

generate, for the each of the first test components, a first preliminary ROI based on the corresponding second locating point;

obtain, for the each of the first test components, a first ROI based on the first preliminary ROI; and analyze performance of the imaging device based on the obtained first ROIs for the plurality of the first test components.

16. The system of claim 15, to generate the first test image based on the image data and the at least one positioning parameter, the at least one processor is further configured to cause the system to:

determine a first locating point based on the at least one positioning parameter, and structural information of the phantom indicating the location of the first test component in the phantom; and generate the first test image based on the first locating point, wherein the first locating point is set as a reconstruction center of the first test image.

17. The system of claim 11, wherein:

the scanned first part of the phantom further includes at least part of a second test component, and the at least one processor is further configured to cause the system to:

obtain a second test image showing a scanned portion of a second test device, the second test device including the second test component;

determine a second ROI relating to the second test component in the second image based on the at least one positioning parameter; and analyze performance of the imaging device based on the first ROI and the second ROI.

18. The system of claim 11, wherein:

the phantom further includes a second part that includes a third test component, the received image data relates to the scanning of both the first part and the second part of the phantom, and the at least one processor is further configured to cause the system to:

generate a third test image based on the received image data and the at least one positioning parameter;

determine a third ROI relating to the third test component in the third test image based on the at least one positioning parameter; and analyze performance of the imaging device based on the first ROI and the third ROI.

19. The system of claim 18, wherein:

the at least one positioning parameter includes a first reference point corresponding to a first point within the first part of the phantom, a first slope of the phantom relative to a first direction, a second slope of the phantom relative to a second direction, and a third slope of the phantom relative to a third direction; and to determine the third ROI based on the at least one positioning parameter, the at least one processor is further configured to cause the system to:

determine a second reference point corresponding to a point within the second part of the phantom based on the first reference point, the second slope, the third slope, and structural information of the phantom indicating the location of the second point relative to the first point; and generate the third test image based on the second reference point and the first slope, wherein the cross section of the phantom at which the second point locates cuts through the third test component.

20. A non-transitory computer-readable medium embodying a computer program product, the computer program product comprising instructions configured to cause a computing device to perform a method comprising:

receiving image data related to a scanning, by the scanner, of a first part of a phantom, the first part of the phantom including at least part of a first test component, and the first test component being used for analyzing imaging performance of the imaging system;

obtaining at least one positioning parameter indicative of a positioning manner of the phantom during the scanning;

generating a first test image based on the received image data; and determining a first region of interest (ROI) related to the first test component in the first test image based on the at least one positioning parameter.

* * * * *